United States Patent [19]

Nakama et al.

[11] Patent Number: 5,785,961
[45] Date of Patent: Jul. 28, 1998

[54] MIXING-AT THE TIME OF USE-TYPE HAIR-TREATING COMPOSITION

[75] Inventors: Yasunari Nakama; Yoko Takeshita; Yasuhiro Arai; Michihiro Yamaguchi; Masa'aki Yasuda, all of Yokohama, Japan

[73] Assignee: Shiseido Company, Ltd., Tokyo, Japan

[21] Appl. No.: 750,115

[22] PCT Filed: Aug. 1, 1995

[86] PCT No.: PCT/JP95/01527

§ 371 Date: Nov. 26, 1996

§ 102(e) Date: Nov. 26, 1996

[87] PCT Pub. No.: WO96/29976

PCT Pub. Date: Oct. 3, 1996

[30] Foreign Application Priority Data

Mar. 28, 1995 [JP] Japan ................................ 7-069099
Mar. 28, 1995 [JP] Japan ................................ 7-069100
Mar. 28, 1995 [JP] Japan ................................ 7-069101

[51] Int. Cl.$^6$ .................................................. A61K 7/06
[52] U.S. Cl. ........................... 424/70.19; 424/70.1; 8/405
[58] Field of Search ............................ 424/401, 70.19, 424/70.1; 8/405

[56] References Cited

U.S. PATENT DOCUMENTS 3,041,244 6/1962 Feit et al. .
4,021,538 5/1977 Yu et al. .
4,776,855 10/1988 Pohl et al. .
5,143,518 9/1992 Madrange et al. .
5,376,146 12/1994 Casperson et al. .
5,393,305 2/1995 Cohen et al. .
5,637,115 6/1997 Balzer et al. .

OTHER PUBLICATIONS

Answer 17 of 81, 1995:947202, Nakama et al, JP93–333500 93, 12, 27–in house computer abstract pp. 16–17.

Answer 18 of 81, 95–106021, US 93–112161, 93.08.26 Cohen et al–in house computer abstract pp. 17–18.

Answer 30 of 81, 92–033525, Hoffkes et al DE90–4022848 90.07.18–in house computer abstract pp. 27–28.

*Primary Examiner*—Joseph L. Schofer
*Assistant Examiner*—N. Sarofin
*Attorney, Agent, or Firm*—Wenderoth, Lind & Ponack, L.L.P.

[57] ABSTRACT

A hair-treating composition having convenient usability and excellent dyeability or hair-bleachability is provided. The composition having the above excellent properties contains at least one member selected from amphoteric surface active agents or semipolar surface active agents according to circumstances, and cationic polymers, in combination with an anionic surface active agent and a higher fatty acid, and further contains a dye or an alkalinizing agent.

26 Claims, No Drawings

MIXING-AT THE TIME OF USE-TYPE HAIR-TREATING COMPOSITION

TECHNICAL FIELD

This invention relates to a mixing-at the time of use-type hair-treating composition. More specifically, the invention relates to a hair dye composition and a hair-bleaching agent composition each containing particular components in such a state that they are combined.

BACKGROUND ART

Heretofore, as mixing-at the time of use-type (namely, two or more agents are combined at the time of use) hair-treating compositions, particularly hair dyes and hair-bleaching agents, twin pack ones have usually been used, and a typical hair-treating composition is one formed by mixing the first agent containing as a principal agent an oxidation dye including an aromatic amino compound and/or an alkalinizing agent such as ammonia with the second agent containing as a principal agent an oxidizing agent such as hydrogen peroxide at the time of use. This mixture is applied onto hair at the time of use, and therefore the mixture is required to have a viscosity of such a degree that it does not drip from the hair. Thus in prior art, a thickening system at the time of mixing has been obtained by utilizing the crystalline region of an aqueous nonionic surface active agent solution. Namely, a. thickening system has been obtained by diluting the first agent wherein a thick nonionic surface active agent having a concentration equal to or higher than the liquid crystal formation concentration and a lower alcohol are compounded together with a dye or an alkalinizing agent, with the second agent containing an oxidizing agent to adjust the concentration of the surface active agent in the final mixture to its liquid crystal region. However, particularly as to dyeing agents, usual systems wherein nonionic surface active agents and lower alcohols are thick had drawbacks that the hair after dyeing is dry to the touch, and since it becomes liquid crystals at the time of mixing, dispersion of the dye is bad and its dyeability is bad.

On the other hand, for the purpose of providing a hair dye making dyeing of hair or giving it a color tone, and at the same time washing and conditioning possible, a hair dye is proposed which contains a cationic polymer, an anionic surface active agent, and an amphoteric or amphoteric ionic surface active agent, in specific rates, respectively (for example, see Japanese Patent Publication No. 22884/1992).

However, it has been difficult to stably provide such a hair dye or hair-bleaching agent that in the preparation compositions before mixing in a separated form, they are stable in physical properties and exhibit relatively low viscosities, but at the time of use, namely when all the components are mixed, the mixed composition does not drip from the hair, and that it is excellent in desired dyeing or decolorization, and the touch of the hair after deying or decolorization, etc.

For example, as to the above composition wherein a lower alcohol was used, there was a tendency that the touch of hair after such treatment is poor.

Thus, the object of the invention lies in providing such a mixing-at the time of use-type hair-treating composition that from a composition at the time of use wherein respective components are mixed, part or all of the lower alcohol can be removed, and moreover when the respective components are independent with one another or in such a form that they are separated as certain groups, they relatively exhibit low viscosities, but when the respective components are combined to be in a mixed state, the mixture exhibits a moderate viscosity.

DISCLOSURE OF INVENTION

It is known that although it does not belong to the technical field of hair dyes, a composition containing an anionic surface active agent, an amphoteric surface active agent and/or a semipolar surface active agent, and a higher fatty acid has, as a skinwashing agent, a moderate viscosity (For example, see Japanese Laid-open Patent Publication No. 17342/1993 and Japanese Laid-open Patent Publication No. 65596/1994).

The present inventors found that as to the respective components of such a composition, when they are subjected to preparation, together with a dye and a peroxide as essential components of a mixing-at the time of use-type hair dye, respectively alone or in specific combinations, the resultant respective preparations are stable and have relatively low viscosities, but when all of them are mixed, a mixed composition can be provided which exhibits an excessive viscosity for the purpose of use as a hair dye.

Thus, the above object can be attained by providing a mixing-at the time of use-type hair-treating composition, particularly hair dye or hair-bleaching agent composition, by the invention, wherein a dye or alkalinizing agent and an oxidizing agent are combined at the time of use, wherein (a) the composition after the combination comprises a dye (I) or an alkalinizing agent (I'), one or more (II) of surface active agents selected from the group consisting of amphoteric surface active agents and semipolar surface active agents, (II) being optional components), one or more (III) of higher fatty acids, one or more (IV) of anionic surface active agents, an oxidizing agent (V), and water (VII), and (b) before use, components selected from the group consisting of component (I) or the alkalinizing agent (I'), components (II) and (III) are put in such a form that they are separated from component (V).

Further, according to the invention, there is provided a composition containing cationic polymer(s) (VI) as additional component(s), namely a mixing-at the time of use-type hair-treating composition, particularly hair dye or hair-bleaching agent composition wherein a dye or alkalinizing agent and an oxidizing agent are combined at the time of use, wherein (a) the composition after the combination comprises a dye (I) or an alkalinizing agent (I'), one or more (II) of surface active agents selected from the group consisting of amphoteric surface active agents and semipolar surface active agents, (II) being optional component(s), one or more (III) of higher fatty acids, one or more (IV) of anionic surface active agents, an oxidizing agent (V), a cationic polymer (VI) and water (VII), and (b) before use, components selected from the group consisting of component (I) or (I'), (II) and (III) and (IV) are put in such a form that they are separated from components selected from the group consisting of components (V) and (VI).

BEST MODE OF CARRYING OUT THE INVENTION

The term of "mixing-at the time of use-type" used in the invention means such a style that previously prepared, two or more preparations are mixed at the time of use, namely at the time of hair treatment. Thus, the invention is, generally, convenient for application to such a hair dye as called a permanent hair dye, but it can also be applied to a hair-bleaching agent by substituting an alkalinizing agent for the dye.

Therefore, although, for making it concise, the following description is made mainly on application to hair dyes, it should be understood that the description becomes that for hair-bleaching agents by substituting alkalinizing agents for the dyes.

As dyes (component (I)) used in the invention, there can be mentioned dye precursors coloring by oxidation of the compounds themselves, and combinations of a dye precursor with a coupler giving various color tones by combination with the dye precursor. Although not limited thereto, as specific examples of such dyes, there can be mentioned 5-aminoorthocresol (another name paraaminoorthocresol), 2-amino-4-nitrophenol, 2-amino-5-nitrophenol, 1-amino-4-methylaminoanthraquinone, 3,3'-iminodiphenol, 2,4-diaminophenol hydrochloride, toluene-2,5-diamine hydrochloride, nitroparaphenylenediamine hydrochloride, paraphenylenediamine hydrochloride, N-phenylparaphenylenediamine hydrochloride, metaphenylenediamine hydrochloride, orthoaminophenol, N-phenylparaphenylenediamine acetate, 1,4-diaminoanthraquinone, 2,6-diaminopyridine, diphenylamine, toluene-2,5-diamine, toluene-3,4-diamine, nitroparaphenylenediamine, paraaminophenylsulfamic acid, paraaminophenol, paranitroorthophenylenediamine, paraphenylenediamine, paramethylaminophenol, N,N'-bis(4aminophenyl)-2,5-diamino-1,4-quinonediimine (another name Bandrofsky base), sodium 2-hydroxy-5-nitro-2',4'-diaminoazobenzene-5-sulfonate (another name Chrome Brown RH), N-phenylparaphenylenediamine, metaaminophenol, metaphenylenediamine, 5-aminoorthocresol sulfate (another name paraaminoorthocresol sulfate), 2-amino-5-nitrophenol sulfate, 4,4'-diaminodiphenylamine sulfate, toluene-2,5-diamine sulfate, nitroparaphenylenediamine sulfate, paraaminophenol sulfate, paranitroorthophenylenediamine sulfate, paranitrometaphenylenediamine sulfate, paraphenylenediamine sulfate, paramethylaminophenol sulfate, metaaminophenol sulfate, metaphenylenediamine sulfate, and/or hematein called a vegetable dye, tannic acid and aromatic polyhydric alcohols such as catechol and resorcinol The above dyes are appropriately used in accordance with desired dyeing color, and in some case, they can be used in combination. The compounding amount of the dye is usually 0.001 to 10 weight %, preferably 0.01 to 5 weight %.

In the hair-bleaching agent composition, at least one of various inorganic and organic alkalis can be used as an alkalinizing agent (component (T)), in place of the above dye. These alkalinizing agents can appropriately be used in accordance with desired bleaching effect, and can be used so as to make the system a pH of 6 to 12.

On the other hand, as the oxidizing agent (component (V)), any one can be used so long as it is such a compound or system that when contacted with the above oxidation dye, it acts so as to bring about coloring based on the dye, and in the hair-bleaching agent composition, when contacted with an alkalinizing agent, it acts so as to bring about bleaching of hair, and the object of the invention is not badly influenced. Usually, it is preferred to use hydrogen peroxide as such a compound. Further, as the above system, there can be used an oxidation-reduction system wherein hydrogen peroxide and ammonium persulfate or another persulfate are combined or an oxidation-reduction system wherein hydrogen peroxide and sodium pyrosulfite are combined, which acts so as to accelerate bleaching (or) decolorization of hair as well as coloring of the dye. In such a system, hydrogen peroxide is put before use in such a form that it is separated from another peroxide, etc.

The use amount of the oxidizing agent cannot be limited because its optimum amount is varied depending on the kind of dyes used, the kind of each component constituting the mixed composition at the time of use and the pH, but when hydrogen peroxide is used, it is preferred to select the use amount so as to be generally 0.2 to 20 weight %, preferably 1 to 5 weight % based on the whole weight of the composition.

In the invention, as to amphoteric surface active agents (component (II)) optionally used, any ones can be used so long as they are amphoteric surface active agents used in usual cosmetic bases, etc. As specific examples thereof, there can be mentioned amidobetaine-type amphoteric surface active agents represented by the general formula (A)

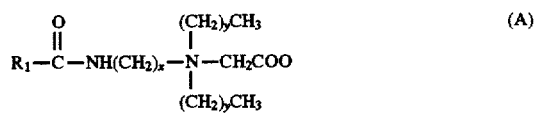

[as products on the market, Revon 2000 (produced by Sanyo Kasei Co.), Anon BDF (produced by Nippon Oil & Fats Co.), etc. are referred to], amidosulfobetaine-type amphoteric surface active agents represented by the general formula (B)

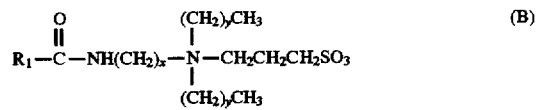

[as products on the market, Ronzaine-CS (Produced by Ronza Co.), Miratine CBS (Produced by Miranol Co.), etc. are referred to], betaine-type amphoteric surface active agents represented by the general formula (C)

[as products on the market, Anon BL (produced by Nippon Oil & Fats Co.), Dehynton AB-30 (produced by Henkel Co.), etc. are referred to], sulfobetaine-type amphoteric surface active agents represented by the general formula (D)

[as products on the market, Ronzaine-12CS (Produced by Ronza Co.), etc. are referred to], imidazolinium-type amphoteric surface active agents represented by the general formula (E)

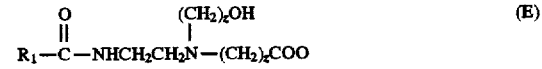

[as products on the market, Ovazoline 662-N (Produced by Toho Chemical Industry Co.), Anon GLM (Produced by Nippon Oil & Fats Co.), etc. are referred to], etc.

Further, as semipolar surface active agents (component (II)) optionally used, there can be exemplified tertiary amine oxide-type semipolar surface active agents represented by the general formula (F)

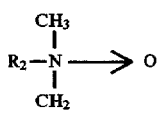

(F)

[as products on the market, Unisafe A-LM (Produced by Nippon Oil & Fats Co.), Wandamin OX-100 (Produced by Shinnippon Rika Co.), etc. are referred to], etc.

In this connection, in the general formulae (A) to (F), $R_1$ is preferably an alkyl group or alkenyl group having on average 9 to 21 carbon atoms, more preferably an alkyl group or alkenyl group having on average 11 to 17 carbon atoms, most preferably an alkyl group or alkenyl group having on average 11 to 13 carbon atoms. When the average carbon number is under 9, hydrophilic properties are stronger compared with the case of 9 or more, and there is a tendency that the thickening action of final products becomes lower. On the other hand, when it exceeds 21, solubility into water becomes bad compared with the case of 21or less, and there is a tendency that the phase separation of these components occurs in the final mixture composition or in preparations before use containing these components, and thus the stability of the compositions becomes bad.

$R_2$ represents an alkyl group or alkenyl group having on average 10 to 18 carbon atoms. x is an integer of 2 to 4, y is an integer of 0 to 3, and z is an integer of 1 or 2.

In the invention, any one or two or more of these amphoteric surface active agents and semipolar surface active agents can be selected and used. As preferred ones among combinations of two or more, there can be mentioned combinations of imidazoliniumbetaine-type amphoteric surface active agent(s) with at least one of other types.

Specifically, it is preferred to use combinations of at least one of imidazoliniumbetaine-type amphoteric surface active agents with at least one selected from the group consisting of amidobetaine-type amphoteric surface active agents, amidosulfobetaine-type amphoteric surface active agents, sulfobetaine-type amphoteric surface active agents and tertiary amine oxide-type semipolar surface active agents.

As stated later, there is a case where when a specific kind of anionic surface active agents used in combination is selected, it is not always necessary to incorporate the above components in the hair-treating composition of the invention.

As higher fatty acids (component (III)) used in the invention, any ones can be used so long as they are higher fatty acids, for example, represented by the following general formula (G), and being used in usual cosmetic bases, etc. General formula (G)

$$R_3COOH \qquad (G)$$

Herein, $R_3$ is preferably a saturated or unsaturated hydrocarbon having a straight chain or branched chain having on average 7 to 25 carbon atoms or a mercury group, more preferably a saturated or unsaturated hydrocarbon having a straight chain or branched chain having on average 9 to 23 carbon atoms or a hydroxyl group, most preferably a saturated or unsaturated hydrocarbon having a straight chain or branched chain having on average 11 to 21 carbon atoms or a hydroxyl group. When the average carbon number is under 7, thickening action at the time of mixing is weak compared with the cases of 7 or more. On the other hand, when it exceeds 25, the solubility in the first agent is small, phase separation occurs and the system becomes highly viscous, compared with the cases of 25 or more.

As specific examples of higher fatty acids, there can be mentioned saturated fatty acids such as lauric acid, myristic acid, palmitic acid, stearic acid, arachic acid and behenic acid; unsaturated fatty acids such as 2-palmitoleic acid, petroselinic acid, oleic acid, elaidic acid, ricinolic acid, linolic acid, linoelaidic acid, linolenic acid and arachidonic acid; branched fatty acids such as isostearic acid; hydroxycarboxylic acids such as 12-hydroxystearic acid; etc. Among them, in view of stability and stimulus properties on skin, saturated fatty acids having 18 carbon atoms, particularly ones having a branch are preferred, and fatty acids which are liquid at room temperature, for example, a saturated fatty acid having 18 carbon atoms and a methyl branch and oleic acid are more preferred. As products on the market, there can, for example, be mentioned isostearic acid (Emery #871 and #875 (produced by Emery Co.), oleic acid (Extraolein 90 and 99 (produced by Nippon Oil & Fats Co.), etc.

Although the invention is not limited by action mechanism, when such a higher fatty acid is used in combination with the above component (I), the component (II) as an optional component and a later-described anionic surface active agent, the stability at low temperatures of a prepared composition (generally, the first agent) containing them is remarkably heightened, and moreover, the viscosity of the mixed composition at the time of use is significantly heightened.

In the invention, among the above higher fatty acids, any one or two ones are selected and used.

The viscosity of the mixed composition at the time of use is increased as the compounding amount of the higher fatty acid is increased, and, particularly, it is preferred to compound the higher fatty acid in an amount of 0.1 to 5 weight %.

When higher fatty acids being liquid at room temperature such as isostearic acid and oleic acid are used, the above effects are still further increased, and compositions prepared using them were stable even at low temperatures of −5° C. or less.

As anionic surface active agents (component (IV)) usable in the invention, there can, for example, be mentioned fatty acid soaps such as bases for soaps, sodium laurate and sodium palmitate, higher alkyl sulfate ester salts such as sodium lauryl sulfate and potassium lauryl sulfate, POE alkyl ether sulfates such as triethanolammonium POE lauryl sulfate and sodium POE lauryl sulfate, N-acylsarcosine acids such as sodium lauroylsarcosinate, alkyloylalkyltaurine salts such as sodium N-myristoyl-N-methyltaurate and sodium N-lauroyl-N-methyltaurate, higher fatty acid amidosulfonate salts such as sodium cocoylmethyltaurate and sodium laurylmethyltaurate, phosphate ester salts such as sodium POE oleyl ether phosphate and POE stearyl ether phosphate, sulfosuccinate salts such as sodium di-2-ethylhexylsulfosuccinate, sodium monolauroylmonoethanolamidopolyoxyethylenesulfosuccinate and sodium laurylpolypropyleneglycolsulfosuccinate, alkylbenzenesulfonate salts such as sodium linear dodecylbenzenesulfonate, triethanolammonium linear dodecylbenzenesulfonate and linear dodecylbenzenesulfonic acid, N-acylglutamate salts such as monosodium N-lauroylglutamate, disodium N-stearoylglutamate and monosodium N-myristoyl-L-glutamate, higher fatty acid ester sulfate ester salts such as sodium hardened coconut oil fatty acid glycerol sulfate, sulfated oils such as Turkey red oil, POE alkyl ether carboxylates, POE alkyl allyl ether carboxylate salts, α-olefinsulfonate salts, higher fatty acid ester sulfonate salts, secondary alcohol sulfate ester salts, higher fatty acid alkylol amide sulfate ester salts, sodium lauroylmonoethanolamidosuccinate, ditriethanolamine N-palmitoylaspartate, casein sodium, etc.

In this connection, "POE" in the above exemplification means polyoxyethylene, and includes ones wherein the ethylene oxide unit is usually 1 to 20.

Among them, those particularly conveniently usable for heightening the viscosity of the mixed composition at the time of use are POE alkyl ether sulfate salts such as sodium POE lauryl sulfate, triethanolammonium POE lauryl sulfate, triethanolammonium POE myristyl sulfate and sodium POE myristyl sulfate, and alkyloyl-alkyltaurine salts such as N-lauroyl-N-methyltaurine salts and N-myristyl-N-methyltaurine salts, wherein the carbon number of the alkyl chain is any even number in the range of 10 to 18, and further α-olefin sulfonate salts.

When these conveniently usable ones are contained in the hair-treating composition of the invention, the desired objects can be attained without using component (II) together. According to the invention, as to these anionic surface active agents, one or more of them can be used in appropriate combinations, and in preparations before use, they can, for example, be mixed with a dye or an alkalinizing agent, or mixed with an oxidizing agent. Thus, they can be used in such a form that they are mixed with component (II) and component (III) or separated therefrom. In this separated form, a preparation before use can be prepared in such a form that component (IV) is mixed with with an oxidizing agent (V), or a small amount of it is used in combination with component (II) and component (III) and a greater amount of it is put in such a form that it is separated from component (II) and component (III).

As cationic polymers (component (VI)) used as an additive component in the invention, all of cationic polymers used in usual cosmetic bases, etc. can be adopted. As specific examples thereof, there can be exemplified quaternary nitrogen-containing cellulose ether derivatives represented by the general formula (H):

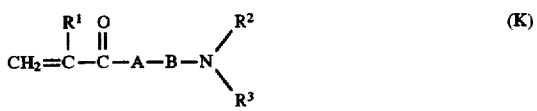

(as products on the market, Polymer JR-400, JR-30M and JR125 (produced by Union Carbide Co.), etc. are referred to), diallyldimethylammonium salt-acrylamide copolymers represented by the general formula (I):

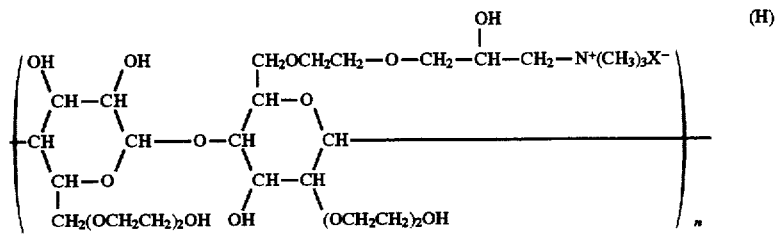

(as products on the market, Marcoat 550 (produced by Merck & Co. and Calgon Co.), etc. are referred to), and poly(diallyldimethylammonium salt) derivatives represented by the general formula (J):

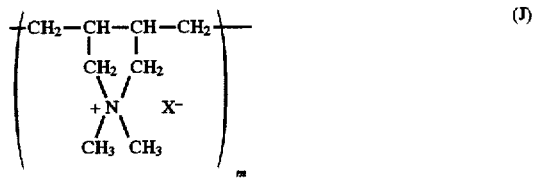

(as products on the market, Marcoat 100 (produced by Merck & Co. and Calgon Co.), etc. are referred to).

As specific examples of the cationic polymer (component (VI)), there can further, for example, be exemplified a cationic copolymer obtained by polymerizing a monomer composition for thickeners containing 15 to 90 weight % of an amine-containing (meth)acrylic monomer represented by the general formula (K):

$$CH_2=C-C-A-B-N\begin{matrix}R^2\\ \\R^3\end{matrix} \quad (K)$$
$$\begin{matrix}R^1 & O & \\ | & || & \end{matrix}$$

(wherein, $R^1$ represents a hydrogen atom or a methyl group, $R^2$ and $R^3$ each independently represent a hydrogen atom, a methyl group, an ethyl group or a tert-butyl group, A represents an oxygen atom or an —NH— group, and B represents an alkylene group of 1 to 4 carbon atoms which is straight-chain or has a side chain), 0 to 80 weight % of a vinyl monomer represented by the general formula (L):

$$CH_2=C-R^4 \quad (L)$$
$$\begin{matrix}R^1\\ |\end{matrix}$$

(wherein, $R^1$ is as defined above, and $R^4$ represents a group represented by the general formula:

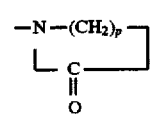

(wherein, p represents 3 or 4) or a group represented by the formula:

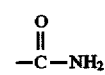

1 to 60 weight % of a (meta)acryloyl group-containing monomer represented by the general formula (M):

(wherein, $R^1$ and A are as defined above, $R^5$ represents an alkylene group of 1 to 17 carbon atoms which is straight-chain or has a side chain, or a group represented by the general formula (N):

(wherein, n represents an integer of 1 to 4, and q represents an integer of 1 to 25), and $R^6$ represents a hydrogen atom or a methyl group), and 0.1 to 25 weight % of a crosslinkable vinyl monomer.

In the invention, among the above cationic polymers, any one or two or more of them are selected and used.

Although thickening effect at the time of mixing is heightened as the compounding amount of the cationic polymer is increased, when the compounding exceeding 5% was made at the time of mixing, the thickening effect is, conversely, lowered. The compounding amount is preferably 0.01 to 5%, and when the thickening effect is taken into account, it is particularly preferably 0.1 to 1%.

When the cationic polymer is used, in view of properties of the peroxide (component (V)) and the cationic polymer (component (VI)), it is desirable in preparations before use of the invention to avoid use in combination of component (I), component (II) as an optional component and component (III) with component (V) and component (VI). Thus, as to the hair dye composition of the invention which is subjected to mixing at the time of mixing, supposing that it is composed of two agents, it is convenient for handling to provide it as a two-agent-type composition wherein the first agent is prepared from component (I), component (II), component (III), component (IV) and water (component VII), and the second agent is prepared from component (V), component (VI) and component (VII).

When a composition at the time of use wherein the respective components are combined and mixed is made to contain, based on the total amount of the components, 5 to 50 weight % of components (IV) and (II), 0.1 to 5 weight % of component (III), and if necessary, 0.01 to 5 weight % of component (VI) as an additional component, it is possible to maintain the viscosity of the preparations before use (for example, the above first agent and the second agent) relatively low (usually, 200 cps or less), and nevertheless it is possible to make the viscosity of the mixed composition at the time of use significantly higher (generally 500 to 10,000 cps, preferably 500 to 5,000 cps, more preferably 1,000 to 3,000 cps). In this connection, the above viscosity means a value measured at 30° C. When the total amount of components (IV) and (II) is under 5%, it is impossible to sufficiently heighten the viscosity of the mixed composition at the time of use, and when the total amount thereof exceeds 50%, the system of the mixed composition comes to exhibit such behavior that liquid crystals are formed, which is not desired.

Further, the weight ratio at the time of mixing of the anionic surface active agent (component (IV)) to the amphoteric surface active agent and/or semipolar surface active agent (component (II)) can be selected so as to be 4/6 to 10/0. In this weight ratio range, high thickening effect can be obtained in a broader pH range (specifically pH 6 to 12) at the time of mixing of the above first agent and the second agent, and thus a hair dye having high dyeability and high uniformity of dyeing on gray or white hair can be obtained.

Further, it also becomes possible to dye hair to bright color so-called dressing up dyeing. Particularly, the hair dye is fit for dyeing of gray or white hair at a pH of 6 or more and under 8, and for dressing up dyeing at a pH of 8 to 12. The first agent and the second agent, and their mixture each exhibit desirable viscosity and stability. It is more desirable to adjust the weight ratio of component (IV)/component (II) to 4/6 to 6/4.

According to the invention, in addition to the above combinations of the respective components, it is also important to make adjustment so that the mixed composition at the time of use can have a pH of 6 to 12. By such adjustment of pH, it becomes possible to maintain the viscosity of the mixed composition (namely, the hair dye composition at the time of use) moderately and moreover heighten dyeing characteristics.

As stated above, according to the invention, when the additional component (VI) is made to be contained a preparation comprising a combination of, at least, component (I) or component (I'), component (II) as an optional component, component (III) and component (VII) is put, before use, in such a form that it is separated from a preparation comprising a combination of component (V), component (VI) and component (VII). Also in this case, it is suitable that the same pH range and use amount of component (IV) and component (II) as in the mixed composition not containing the above component (VI) are adopted.

For making the first agent alkaline, an alkaline pH adjusting agent is compounded. As specific examples of the pH adjusting agent, there can, usually, be mentioned ammonia water, alkanolamines such as monoethanolamine, hydroxides such as sodium hydroxide and potassium hydroxide, carbonates such as sodium carbonate, and silicates such as sodium silicate. Further, there can also be used inorganic ammonium salts such as ammonium sulfate, ammonium nitrate, ammonium chloride, ammonium bicarbonate, ammonium dihydrogenphosphate and diammonium hydrogenphosphate. Further, these can also be used as as a constituent of the alkalinizing agent when the composition of the invention is made as a hair-bleaching agent.

The pH at the time of use of the hair-treating composition of the invention can be adjusted either by compounding a pH adjusting agent before mixing of the first agent with the second agent, or by adding it at the time of mixing. In this connection, "at the time of mixing" means during mixing or after mixing, but it is preferred to make the compounding during the mixing.

Further, in the hair-treating composition of the invention, it is also possible to compound a lower alcohol in such a range that the effects of the invention are not influenced (namely, preferably in an amount of 3 weight % or less in the first agent). As specific examples of the lower alcohol, there can usually be mentioned monohydric alcohols having 2 to 5 carbon atoms such as ethyl alcohol, n-propanol, isopropanol and butanol. In hair dyes, by incorporating a lower alcohol, permeation of the dye into hair is accelerated, but the touch of the hair is lowered thereby, and thus there is often a case where it is preferred not to compound it. On the other hand, since in usual hair dyes, a large amount of a lower alcohol is compounded in the first agent, but in the invention, its content can be made zero or small, the hair dye of the invention can be one excellent in use feeling even at the time of rinsing.

Other hair-protecting agents, stabilizers, perfumes, humectants, etc. can be incorporated into the hair-treating composition of the invention, at the stage of preparations therefor or at the stage of the preparations having been mixed, in such a range that the objects of the invention are not spoiled.

As stated above, the hair-treating composition of the invention including both of the preparations before use and the combination of these preparations at the time of use, when the final product was applied to hair, exhibits excellent dyeing characteristics as a hair dye, without substantially bringing about dropping from the hair. Further, each preparation is excellent in preservation stability and covenient for handling, and further can be provided as a composition having a relatively low viscosity.

The invention is further described below according to specific examples. Parts or percentages (%) used in the examples mean (weight/weight) parts or (weight/weight) % unless otherwise defined.

First, methods for evaluating the effects of the invention are shown.

1) Dyeability test using hair strands

Hair strands (2 g) previously bleach (decolorization)-treated were coated with 10 g of a hair dye, and evaluation was made based on the relations between time for which the hair strands were left alone and the L value. In this connection, the L value means the value of L in the color difference equation of Hunter.

2) Comparative test on dyeability and dryness to the touch by a panel of experts A series of hair dyeing operations was conducted, and dyeability of the hair and dryness to the touch after drying were evaluated according to the following criterion, using a panel of 10 experts. <Dyeability>

++ . . . Dyeability is remarkably good and the hair is uniformly dyed

+ . . . Dyeability is good and the hair is uniformly dyed

± . . . Dyeability is a little poor

− . . . The hair is unevenly dyed and there is no dyeability <Dryness to the touch>

++ . . . The hair is not dry to the touch and gives smooth touch

+ . . . The hair is not dry to the touch

± . . . The hair is a little dry to the touch

− . . . The hair is strikingly dry to the touch

3) Viscosity of mixed solution

The first agent and the second agent were mixed and the viscosity of the mixed solution was measured at 30° C. using a Brook-field type viscometer.

4) Low temperature stability

The first agent (100 g) was stored in a constant temperature bath of −5° C. for one month, and the state thereof was visually observed and evaluated according to the following criterion.

++ . . . Any change is not observed at all compared with the initial state

+ . . . Any change is not observed at all compared with the initial state, but there is a slight increase of the viscosity ± . . . A slight turbidity is formed − . . . Separation occurs

EXAMPLE 1 AND COMPARATIVE EXAMPLE 1 (USUAL SYSTEM)

In the following example, the effects of the composition of the invention in the case where an anionic surface active agent is used in mixing with an oxidizing agent are illustrated.

The following first agent and the second agent of the invention or a usual system were mixed in a ratio of 1:1 to prepare a hair dye, and using hair strands, the difference in dyeability between the invention and the usual system was evaluated based on relations between time for which the hair strands were left alone and the L value.

Further, the viscosities of the first agent and the second agent, and the viscosity after mixing of both were measured.

Example 1

|  | (weight %) |
|---|---|
| (The first agent) | |
| Undecyl-N-hydroxyethyl-N-carboxymethylimidazolinium betaine | 3.0 |
| Cocoyl Amide Propyldimethyl Glycine | 7.0 |
| Oleic acid | 3.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Perfume | Appropriate amount |
| Purified water | Balance |
| Total | 100.0 |
| (The second agent) | |
| Sodium Polyoxyethylene (1.5) alkyl (12, 14) ether sulfate | 10.0 |
| Aqueous hydrogen peroxide | 20.0 |
| Methylparaben | Appropriate amount |
| Sodium stannate | Appropriate amount |
| Phosphate buffer | Adjusted to pH 3 |
| Purified water | Balance |
| Total | 100.0 |

Comparative Example 1

|  | (weight %) |
|---|---|
| (The first agent) | |
| Polyoxyethylene (2) oleyl ether | 15.0 |
| Polyoxyethylene (5) octylphenyl ether | 5.0 |
| Oleic acid | 10.0 |
| Monoethanolamine | 2.0 |
| Ammonia water (28%) | 10.0 |
| Paraphenylenediamine | 1.0 |
| Resorcinol | 1.0 |
| L-ascorbic acid | 0.5 |
| Sodium hydrosulfite | 0.1 |
| Perfume | Appropriate amount |
| Purified water | Balance |
| Total | 100.0 |
| (The second agent) | |
| Aqueous hydrogen peroxide (30%) | 20.0 |
| Methylparaben | Appropriate amount |
| Sodium stannate | Appropriate amount |
| Phosphate buffer | Adjusted to pH 3 |
| Purified water | Balance |
| Total | 100.0 |

The L value at 20 minutes after the treatment with the hair dye of Example 1 was 14.6 and that in the case of the comparative example was 16.9, and also by visual observation, the product of the invention was superior to the usual system in dyeability.

Next, the dyed hair was irradiated with carbon arc for 20 hours or with a xenon lamp for 30 hours, and change of L values (ΔL) was checked. In Comparative example 1, ΔL was 12.2 (xenon), whereas in the present example, ΔL was 3.6 (xenon), and the hair dyed with the present example was found to be slow to discolor.

Further, as to the first agent of Example 1, the pH was 10.65 and the viscosity was 150 cps, and as to the second agent, the pH was 3.0 and the viscosity was 12 cps, and after both were mixed, the pH became 9.3 and the viscosity became 4,200 cps, and remarkable thickening effect was observed.

Next, the first agent and the second agent of Example 1 were used, and an appropriate amount of a pH-adjusting agent (ammonia water or phosphoric acid) was added at the time of mixing to prepare hair dyes of pH 5, 6 and 12, respectively. When viscosity was measured, the viscosities of these hair dyes were 460 cps, 2,510 cps and 890 cps, respectively, and it was found that in hair dyes of the invention wherein the pH is 6 to 12, excellent thickening effect can be obtained. Further, the L values at 20 minutes after the hair dyeing treatment were 52, 23 and 38, respectively, and it was revealed that dyeability is high in the range of pH 6 to 12.

Examples 2 to 25 and Comparative Examples 2 to 9

Evaluation was made according to the above evaluation method on hair dyes obtained by mixing the first agents and the second agents each having various compositions. The results are shown together in Tables 1 to 4. In the following tables, the expression "to 100" means purified water is added upto 100 weight %.

TABLE 1

|  | Example 2 | Example 3 | Example 4 | Example 5 | Example 6 | Example 7 | Example 8 | Example 9 |
|---|---|---|---|---|---|---|---|---|
| (The first agent) | | | | | | | | |
| Undecyl-N-hydroxy-N-carboxy-methylimidazolinium betaine | 8 | — | 2 | 3 | 4 | 8 | 15 | 4 |
| Cocoyl Amide Propyldimethyl Glycine | — | — | 8 | 12 | — | 7 | 3 | 2.66 |
| Sodium Lauroamphoacetate | — | — | — | — | 6 | — | — | — |
| Oleic acid | 2 | 3 | 3 | 3 | 3 | 3 | 4 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 10 | 15 | 10 | 15 | 10 | 15 | 15 | 10 |
| L-ascorbic acid | 0.5 | 0.5 | 0.5 | 0.5 | 0.5 | 0.5 | 0.5 | 0.5 |
| Sodium hydrosulfite | — | 0.1 | — | — | 0.1 | — | 0.1 | — |
| Paraphenylenediamine | 1 | 1 | 0.5 | 1 | 1 | 1 | 1.5 | 0.8 |
| Resorcinol | — | 1 | 0.2 | 0.5 | 0.5 | 1 | 0.8 | 0.4 |
| Purified water | to 100 | to 100 | to 100 | to 100 | to 100 | to 100 | to 100 | to 100 |
| (The second agent) | | | | | | | | |
| Triethanolammonium polyoxyethylene (2) alkyl (12,14) ether sulfate | 8 | 10 | 15 | 10 | 10 | 10 | 9 | 15 |
| Sodium α-alkenyl (12,13) sulfonate | — | — | — | — | — | — | — | — |
| Sodium lauroylmethyltaurate | — | — | — | — | — | — | — | — |
| O-[2-hydroxy-3-(trimethylammonio)-propyl]hydroxyethylcellulose chloride | — | — | — | — | — | — | — | — |
| Dimethylmethylenepiperidinium polychloride | — | — | — | — | — | — | — | — |
| Dimethylallyammonium chloride-acrylamide copolymer | — | — | — | — | — | — | — | — |
| Vinylpyrrolidone-N,N-dimethylaminoethyl methacrylate-stearyl acrylate-tripropylene glycol diacrylate copolymer | — | — | — | — | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/2 | 1.5/1 |
| Weight ratio (anionic surface active agent/amphoteric surface active agent) | 5/5 | 10/0 | 6/4 | 4/6 | 5/5 | 5/5 | 5/5 | 4/6 |
| pH at the time of mixing | 9.5 | 9.8 | 9.2 | 9.5 | 9.2 | 9.2 | 9 | 9.4 |
| Dyeability | ++ | ++ | ++ | ++ | ++ | ++ | ++ | ++ |
| Dryness to the touch | ++ | ++ | ++ | ++ | ++ | ++ | ++ | ++ |
| Viscosity of the first agent | 100 | 120 | 110 | 150 | 130 | 130 | 150 | 110 |
| Viscosity of the second agent | 40 | 40 | 40 | 55 | 45 | 50 | 40 | 40 |
| Viscosity after mixing | 3000 | 2500 | 5000 | 2800 | 3800 | 1900 | 2300 | 1500 |
| Low temperature stability | ++ | ++ | ++ | ++ | ++ | ++ | ++ | ++ |

TABLE 2

|  | Example 10 | Example 11 | Example 12 | Example 13 | Example 14 | Example 15 | Example 16 | Example 17 |
|---|---|---|---|---|---|---|---|---|
| (The first agent) | | | | | | | | |
| Undecyl-N-hydroxy-N-carboxy-methylimidazolinium betaine | 2 | 1 | 2 | 2 | 2 | 5 | 4 | 6 |
| Cocoyl Amide Propyldimethyl Glycine | 6 | 9 | 6 | 4 | 10 | 10 | 6 | 6 |
| Sodium Lauroamphoacetate | — | — | — | 2 | — | — | — | — |
| Oleic acid | 2 | 3 | 3 | 3 | 3 | 3 | 3 | 2 |
| Isostearic acid (Emery #871 desalted product) | — | — | — | — | — | — | — | 1 |
| Monoethanolamine | 1 | 2 | 2 | 2 | 2 | 2 | 2.5 | 3 |
| Ammonia water (28%) | 10 | 10 | 10 | 10 | 12 | 10 | — | — |
| L-ascorbic acid | 0.5 | 0.5 | 0.5 | 0.5 | 0.5 | 0.5 | 0.5 | 0.5 |
| Paraphenylenediamine | 1 | 1 | 0.5 | 1 | 1 | 1 | 1 | 1 |
| Resorcinol | — | 1 | 1 | 1 | 1 | 1 | 0.5 | 1 |
| 1,3-Butylene glycol | 2 | 1 | 3 | 2 | 1.5 | 2 | 4.5 | 4 |
| Ethanol | — | — | — | — | — | 2 | — | — |
| Purified water | to 100 | to 100 | to 100 | to 100 | to 100 | to 100 | to 100 | to 100 |
| (The second agent) | | | | | | | | |
| Triethanolammonium polyoxyethylene (2) alkyl (12,14) ether sulfate | 8 | 10 | 10 | — | — | — | 5 | 5 |
| Sodium α-alkenyl (12,13) sulfonate | — | — | 2 | 8 | 8 | 10 | — | 3 |
| Sodium lauroylmethyltaurate | — | — | — | — | — | — | 5 | — |
| O-[2-hydroxy-3-(trimethylammonio)-propyl]hydroxyethylcellulose chloride | — | — | 0.5 | — | — | — | — | — |
| Dimethylmethylenepiperidinium polychloride | 0.5 | — | — | — | — | — | — | — |
| Dimethylallyammonium chloride-acrylamide copolymer | — | — | — | 0.3 | — | — | — | — |
| Vinyl pyrrolidone-N,N-dimethylaminoethyl methacrylate-stearyl acrylate-tripropylene glycol diacrylate copolymer | — | — | — | — | — | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/1 | 1/1 |
| Weight ratio (anionic surface active agent/amphoteric surface active agent) | 5/5 | 5/5 | 6/4 | 5/5 | 6/4 | 5/5 | 5/5 | 6/4 |
| pH at the time of mixing | 9.5 | 9.3 | 9.2 | 9.3 | 9.5 | 9.5 | 7.5 | 7.8 |
| Dyeability | ++ | ++ | ++ | ++ | ++ | ++ | ++ | ++ |
| Dryness to the touch | ++ | ++ | ++ | ++ | ++ | ++ | ++ | ++ |
| Viscosity of the first agent | 100 | 120 | 110 | 80 | 130 | 110 | 120 | 150 |
| Viscosity of the second agent | 40 | 40 | 40 | 30 | 40 | 30 | 40 | 40 |
| Viscosity after mixing | 3000 | 5500 | 7000 | 4500 | 3500 | 2500 | 8500 | 6400 |
| Low temperature stability | ++ | ++ | ++ | ++ | ++ | ++ | ++ | ++ |

TABLE 3

|  | Example 18 | Example 19 | Example 20 | Example 21 | Example 22 | Example 23 | Example 24 | Example 25 |
|---|---|---|---|---|---|---|---|---|
| (The first agent) | | | | | | | | |
| Undecyl-N-hydroxy-N-carboxy-methylimidazolinium betaine | 2 | 2 | 2 | 2 | 1 | 5 | 5 | 2 |
| Cocoyl Amide Propyldimethyl Glycine | 6 | — | 8 | 2 | 4 | 2 | 11 | 8 |
| Sodium Lauroamphoacetate | — | — | — | — | — | 3 | — | — |
| Oleic acid | 3 | 3 | 3 | 3 | 3 | 3 | 3 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 15 | 10 | 5 | 10 | 10 | 10 | 11 | 6 |
| L-ascorbic acid | 0.5 | 0.5 | 0.5 | 0.5 | 0.5 | 0.5 | 0.5 | 0.5 |

TABLE 3-continued

|  | Example 18 | Example 19 | Example 20 | Example 21 | Example 22 | Example 23 | Example 24 | Example 25 |
|---|---|---|---|---|---|---|---|---|
| Paraphenylenediamine | 1 | 1 | 1 | 1 | 0.5 | 1 | 0.5 | 1 |
| Resorcinol | 0.5 | 1 | 1 | 0.5 | 1 | 1 | 1 | 1 |
| 1,3-Butylene glycol | 1 | 0.5 | 3 | 1 | 0.5 | 2 | 0.5 | 2.5 |
| Ethanol | — | — | — | — | — | — | — | 0.5 |
| Purified water | to 100 | to 100 | to 100 | to 100 | to 100 | to 100 | to 100 | to 100 |
| (The second agent) | | | | | | | | |
| Triethanolammonium polyoxyethylene (2) alkyl (12,14) ether sulfate | 2 | — | 8 | 4 | 1 | 6 | — | 5 |
| Sodium α-alkenyl (12,13) sulfonate | 8 | 18 | 2 | 12 | 4 | — | 10 | 5 |
| Sodium lauroylmethyltaurate | — | — | — | — | — | 4 | — | — |
| O-[2-hydroxy-3-(trimethylammonio)-propyl]hydroxyethylcellulose chloride | — | — | — | — | — | — | — | — |
| Dimethylmethylenepiperidinium polychloride | — | — | — | — | — | — | — | — |
| Dimethylallyammonium chloride-acrylamide copolymer | — | — | — | — | — | — | — | — |
| Vinyl pyrrolidone-N,N-dimethylaminoethyl methacrylate-stearyl acrylate-tripropylene glycol diacrylate copolymer | — | — | — | — | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1.5 | 1/1 |
| Weight ratio (anionic surface active agent/amphoteric surface active agent) | 5/5 | 9/1 | 6/4 | 8/2 | 5/5 | 5/5 | 5/5 | 5/5 |
| pH at the time of mixing | 11.5 | 9.3 | 8.3 | 9.4 | 9.2 | 9.3 | 9.4 | 9 |
| Dyeability | ++ | ++ | ++ | ++ | ++ | ++ | ++ | ++ |
| Dryness to the touch | + | ++ | ++ | ++ | ++ | ++ | ++ | ++ |
| Viscosity of the first agent | 90 | 60 | 120 | 80 | 70 | 100 | 180 | 120 |
| Viscosity of the second agent | 30 | 40 | 45 | 35 | 20 | 30 | 40 | 40 |
| Viscosity after mixing | 1200 | 3500 | 7000 | 2800 | 600 | 800 | 4500 | 5400 |
| Low temperature stability | ++ | ++ | ++ | ++ | ++ | ++ | ++ | ++ |

TABLE 4

|  | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|
| (The first agent) | | | | | | | | |
| Undecyl-N-hydroxy-N-carboxy-methylidazolinium betaine | 14 | — | 7 | — | 5 | 10 | 2 | 8 |
| Cocoyl Amide Propyldimethyl Glycine | — | 14 | — | — | 5 | — | 6 | 6 |
| Sodium Lauroamphoacetate | — | — | — | — | — | — | — | — |
| Oleic acid | 2 | 3 | 3 | — | 3 | 3 | — | 2 |
| Sodium polyoxyethylene (1,5) alkyl (12,14) ether sulfate | — | — | — | — | — | — | — | — |
| Polyoxyethylene (2) oleyl ether | — | — | 5 | 5 | — | 5 | — | — |
| Polyoxyethylene (5) octylphenyl ether | — | — | — | — | — | 5 | — | — |
| Sodium alkylbenzenesulfonate | — | — | — | — | — | — | — | 5 |
| Isostearic acid (Emery #871 desalted product) | — | — | — | — | — | — | — | 1 |
| Monoethanolamine | 1 | 2 | 2 | 2 | 2 | 2 | 2 | 3 |
| Ammonia water (28%) | 10 | 10 | 10 | 10 | 12 | 10 | 10 | 10 |
| L-ascorbic acid | 0.5 | 0.5 | 0.5 | 0.5 | 0.5 | 0.5 | 0.5 | 0.5 |
| Paraphenylenediamine | 1 | 1 | 0.5 | 1 | 1 | 1 | 1 | 1 |
| Resorcinol | — | 1 | 1 | 1 | 1 | 1 | 0.5 | 1 |
| 1,3-Butylene glycol | — | — | — | — | — | — | — | — |
| Ethanol | — | — | — | — | — | — | — | 10 |
| Isopropanol | 8 | — | — | — | — | — | — | — |

TABLE 4-continued

|  | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|
| Purified water (The second agent) | to 100 | to 100 | to 100 | to 100 | to 100 | to 100 | to 100 | to 100 |
| Triethanolammonium polyoxyethylene (2) alkyl (12,14) ether sulfate | 6 | 6 | 3 | 10 | — | — | 8 | 5 |
| Sodium α-alkenyl (12,13) sulfonate | — | — | — | — | — | — | — | 3 |
| Sodium lauroylmethyltaurate | — | — | — | — | — | — | — | — |
| O-[2-hydroxy-3-(trimethylammonio)-propyl]hydroxyethylcellulose chloride | — | — | — | — | — | — | — | — |
| Dimethylmethylenepiperidinium polychloride | — | — | — | — | — | — | — | — |
| Dimethylallyammonium chloride-acrylamide copolymer | — | — | — | — | — | — | — | — |
| Vinylpyrrolidone-N,N-dimethylaminoethyl methacrylate-stearyl acrylate-tripropylene glycol diacrylate copolymer | — | — | — | — | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1 | 1/1 |
| Weight ratio (anionic surface active agent/amphoteric surface active agent) | 3/7 | 3/7 | 3/7 | 10/0 | 0/10 | 0/10 | 5/5 | 4/6 |
| pH at the time of mixing | 9.4 | 9.5 | 9.2 | 9.8 | 9.8 | 9.3 | 9.8 | 9.8 |
| Dyeability | ++ | ++ | + | + | ± | ± | ++ | + |
| Dryness to the touch | ++ | − | ± | ± | ++ | − | + | − |
| Viscosity of the first agent | 100 | 130 | 110 | 80 | 120 | 100 | 140 | 50 |
| Viscosity of the second agent | 40 | 40 | 30 | 30 | 20 | 30 | 20 | 20 |
| Viscosity after mixing | 200 | 300 | 1000 | 1500 | 200 | 1400 | 1200 | 400 |
| Low temperature stability | ++ | ++ | ± | ± | − | ± | − | + |

As apparent from the above Tables 1 to 4, the hair dyes of the invention are excellent in dyeability, and free from dryness to the touch, and for example, when they are prepared as the first agent and the second agent, they are low in viscosity, respectively, moderate in the viscosity after mixing and moreover excellent in low temperature stability. Further, in all of the hair dyes of the invention, good thickening effect was ascertained, all of them exhibited viscosities of 500 cps or more, and it is seen that they have high thickening effect.

Example 26 and Comparative Example 10 (Usual System)

In the following example, the effects of the composition of the invention in the case where an anionic surface active agent is used in mixing with the first agent are illustrated.

The following first agent and the second agent of the invention or a usual system were mixed in a ratio of 1:1 to prepare a hair dye, and using hair strands, the difference in dyeability between the invention and the usual system was evaluated based on relations between time for which the hair strands were left alone and the L value. Further, the viscosities of the first agent and the second agent, and the viscosity after mixing of both were measured.

|  | (weight %) |
|---|---|
| [The first agent] (Example 26) | |
| Sodium polyoxyethylene (1.5) alkyl (12, 14) ether sulfate | 16.0 |
| Undecyl-N-hydroxyethyl-N-carboxymethylimidazolinium betaine | 4.0 |
| Oleic acid | 5.0 |
| Monoethanolamine | 3.0 |
| L-ascorbic acid | 0.5 |
| Paraphenylenediamine | 1.0 |
| Resorcinol | 1.0 |
| Perfume | Appropriate amount |
| Purified water | Balance |
| Total | 100.0 |
| [The first agent] (Comparative example 10) | |
| Polyoxyethylene (2) oleyl ether | 15.0 |
| Polyoxyethylene (5) octylphenyl ether | 5.0 |
| Oleic acid | 10.0 |
| Monoethanolamine | 3.0 |
| Paraphenylenediamine | 1.0 |
| Resorcinol | 1.0 |
| L-ascorbic acid | 1.5 |
| Sodium sulfite | 0.1 |

-continued

| | (weight %) |
|---|---|
| Perfume | Appropriate amount |
| Purified water | Balance |
| Total | 100.0 |

[The second agent]

| | |
|---|---|
| Aqueous hydrogen peroxide (30%) | 20.0 |
| Methylparaben | Appropriate amount |
| Sodium stannate | Appropriate amount |
| Phosphate buffer | Adjusted to pH 2 |
| Purified water | Balance |
| Total | 100.0 |

The L value at 20 minutes after the treatment with Example 26 was 13.2 and that in the case of the comparative example was 16.5, and also by visual observation, the product of the invention was found to be superior to the usual system in dyeability.

Next, the dyed hair was irradiated with carbon arc for 20 hours or with a xenon lamp for 30 hours, and change of L values (ΔL) was checked. In Comparative example 10, ΔL was 12.0 (xenon), whereas in Example 26, ΔL was 6.0 (xenon), and the hair dyed with the present example was found to be slow to discolor.

Further, as to the first agent of Example 26, the pH was 9.83 and the viscosity was 300 cps, and as to the second agent, the pH was 2.1 and the viscosity was 10 cps, and after both were mixed, the pH became 7.8 and the viscosity became 7,200 cps, and remarkable thickening effect was observed.

Next, the first agent and the second agent of Example 26 were used, and an appropriate amount of a pH-adjusting agent (ammonia water or phosphoric acid) was added at the time of mixing to prepare hair dyes of pH 5, 6 and 12, respectively. When viscosity was measured, the viscosities of these hair dyes were 400 cps, 3,000 cps and 1,070 cps, respectively, and it was found that in the hair dyes of the invention wherein the pH is 6 to 12, excellent thickening effect can be obtained. Further, the L values at 20 minutes after the hair dyeing treatment were 45, 20 and 20, respectively, and it was revealed that dyeability is high in the range of pH 6 to 12.

Examples 27 to 39 and Comparative Examples 11 to 24

Evaluation was made according to the above-mentioned evaluation method on hair dyes obtained by mixing the first agents having various compositions with the second agent used in Example 26. The results are shown together in Tables 5 to 9.

TABLE 5

| (The first agent) | Example 27 | Example 28 | Example 29 | Example 30 | Example 31 |
|---|---|---|---|---|---|
| Triethanolammonium polyoxyethylene (2) alkyl (12,14) ether sulfate | 8 | 10 | 12 | 18 | 16 |
| Polyoxyethylene (2) oleyl ether | — | — | — | — | — |
| Polyoxyethylene (5) octylphenyl ether | — | — | — | — | — |
| Undecyl-N-hydroxy-N-carboxymethylimidazolinium betaine | 2 | — | 4 | — | 4 |
| Cocoyl Amide Propyldimethyl Glycine | — | — | 4 | 2 | — |
| Sodium Lauroamphoacetate | — | — | — | — | — |
| Oleic acid | 2 | 3 | 3 | 4 | 3 |
| Isostearic acid (Emery #871 desalted product) | — | — | — | — | — |
| Isopropanol | — | — | — | — | — |
| Monoethanolamine | 2 | 2 | 2 | 2 | 1 |
| Ammonia water (28%) | — | 10 | 9 | 1 | 20 |
| L-ascorbic acid | 0.5 | 0.5 | 0.5 | 0.5 | 0.5 |
| Paraphenylenediamine | 1.0 | 1.0 | 1.0 | 1.0 | 1.0 |
| Resorcinol | — | 1.0 | 1.0 | 1.0 | 1.0 |
| Purified water | to 100 | to 100 | to 100 | to 100 | to 100 |
| Weight ratio (anionic surface active agent/amphoteric surface active agent) | 8/2 | 10/0 | 6/4 | 9/1 | 8/2 |
| pH at the time of mixing | 7.2 | 9.1 | 8.2 | 7.3 | 10.5 |
| Dyeability | ++ | ++ | ++ | ++ | ++ |
| Dryness to the touch | ++ | ++ | ++ | ++ | ++ |
| Viscosity after mixing | 7000 | 5500 | 7000 | 5500 | 6000 |
| Low temperature stability | ++ | ++ | ++ | ++ | ++ |

TABLE 6

| (The first agent) | Example 32 | Example 33 | Example 34 | Example 35 | Example 36 |
|---|---|---|---|---|---|
| Triethanolammonium polyoxyethylene (2) alkyl (12,14) ether sulfate | 14 | 15 | 16 | 8 | 14 |
| Sodium lauryl ether sulfate | — | — | — | — | — |
| Polyoxyethylene (2) oleyl ether | — | — | — | — | — |
| Polyoxyethylene (5) octylphenyl ether | — | — | — | — | — |

TABLE 6-continued

| (The first agent) | Example 32 | Example 33 | Example 34 | Example 35 | Example 36 |
|---|---|---|---|---|---|
| Undecyl-N-hydroxy-N-carboxymethylimidazolinium betaine | 2 | — | 1 | 2 | — |
| Cocoyl Amide Propyldimethyl Glycine | — | — | 1 | — | 2 |
| Sodium Lauroamphoacetate | 4 | — | 1 | — | 2 |
| Oleic acid | 2 | 2 | 1 | 3 | 2 |
| Isostearic acid (Emery #871 desalted product) | — | 1 | 1 | — | 1 |
| Isopropanol | — | — | — | — | — |
| Monoethanolamine | 1 | 1 | 2 | 2 | 1 |
| Ammonia water (28%) | 5 | 1 | 10 | 10 | 10 |
| L-ascorbic acid | 0.5 | 0.5 | 0.5 | 0.5 | 0.5 |
| Paraphenylenediamine | 1.0 | 1.0 | 1.0 | 1.0 | 1.0 |
| Resorcinol | — | 1.0 | 1.0 | 1.0 | 1.0 |
| Purified water | to 100 | to 100 | to 100 | to 100 | to 100 |
| Weight ratio (anionic surface active agent/amphoteric surface active agent) | 7/3 | 10/0 | 8/2 | 8/2 | 7/3 |
| pH at the time of mixing | 8.5 | 7.2 | 9.9 | 9.4 | 8.6 |
| Dyeability | ++ | ++ | ++ | ++ | ++ |
| Dryness to the touch | ++ | ++ | ++ | ++ | ++ |
| Viscosity after mixing | 4000 | 5500 | 7000 | 800 | 7500 |
| Low temperature stability | ++ | ++ | ++ | ++ | ++ |

TABLE 7

| (The first agent) | Example 37 | Example 38 | Example 39 |
|---|---|---|---|
| Triethanolammonium polyoxyethylene (2) alkyl (12,14) ether sulfate | 16 | 16 | — |
| Sodium lauryl ether sulfate | — | — | 12 |
| Polyoxyethylene (2) oleyl ether | — | — | — |
| Polyoxyethylene (5) octylphenyl ether | — | — | — |
| Undecyl-N-hydroxy-N-carboxymethylimidazolinium betaine | 2 | 2 | 4 |
| Cocoyl Amide Propyldimethyl Glycine | 2 | 2 | 4 |
| Sodium Lauroamphoacetate | — | — | — |
| Oleic acid | 3 | 3 | 3 |
| Isostearic acid (Emery #871 desalted product) | — | — | — |
| Isopropanol | 1.5 | 3.0 | — |
| Monoethanolamine | 2 | 2 | 2 |
| Ammonia water (28%) | 10 | 10 | 9 |
| L-ascorbic acid | 0.5 | 0.5 | 0.5 |
| Paraphenylenediamine | 1.0 | 1.0 | 1.0 |
| Resorcinol | 0.2 | 0.2 | 0.2 |
| Purified water | to 100 | to 100 | to 100 |
| Weight ratio (anionic surface active agent/amphoteric surface active agent) | 8/2 | 8/2 | 6/4 |
| pH at the time of mixing | 9.0 | 8.9 | 8.5 |
| Dyeability | ++ | ++ | ++ |
| Dryness to the touch | + | + | + |
| Viscosity after mixing | 2300 | 2300 | 2500 |
| Low temperature stability | ++ | ++ | ++ |

TABLE 8

| (The first agent) | Comparative Example 11 | Comparative Example 12 | Comparative Example 13 | Comparative Example 14 | Comparative Example 15 | Comparative Example 16 |
|---|---|---|---|---|---|---|
| Triethanolammonium polyoxyethylene (2) alkyl (12,14) ether sulfate | 10 | 10 | 10 | — | 10 | 16 |
| Triethanolammonium polyoxyethylene (2) alkyl (12,13) ether sulfate | — | — | — | 10 | — | — |
| Polyoxyethylene (2) oleyl ether | — | — | — | — | — | — |
| Polyoxyethylene (5) octylphenyl ether | — | — | — | — | — | — |
| Undecyl-N-hydroxy-N-carboxymethyl imidazolinium betaine | 10 | — | 2 | — | 10 | 2 |
| Cocoyl Amide Propyldimethyl Glycine | — | 10 | 8 | — | — | — |
| Sodium Lauroamphoacetate | — | — | — | — | — | — |
| Oleic acid | 2 | 3 | 3 | — | 3 | 3 |
| Isostearic acid (Emery #871 desalted product) | — | — | — | — | — | — |

TABLE 8-continued

| (The first agent) | Comparative Example 11 | Comparative Example 12 | Comparative Example 13 | Comparative Example 14 | Comparative Example 15 | Comparative Example 16 |
|---|---|---|---|---|---|---|
| Isopropanol | — | — | 5 | — | — | 4 |
| Monoethanolamine | 1 | 1 | 2 | 2 | 1 | 2 |
| Ammonia water (28%) | 12 | 14 | 10 | 10 | 25 | 10 |
| L-ascorbic acid | 0.5 | 0.5 | 0.5 | 0.5 | 0.5 | 0.5 |
| Paraphenylenediamine | 1.0 | 1.0 | 1.0 | 1.0 | 1.0 | 1.0 |
| Resorcinol | — | 1.0 | 1.0 | 1.0 | 1.0 | 0.2 |
| Purified water | to 100 | to 100 | to 100 | to 100 | to 100 | to 100 |
| Weight ratio (anionic surface active agent/amphoteric surface active agent) | 5/5 | 5/5 | 5/5 | 10/0 | 10/0 | 8/2 |
| pH at the time of mixing | 9.4 | 9.5 | 9.2 | 9.8 | 12.5 | 9.0 |
| Dyeability | ++ | ++ | ++ | ++ | ± | ++ |
| Dryness to the touch | ++ | ++ | ± | ± | − | ± |
| Viscosity after mixing | 400 | 350 | 300 | 120 | 280 | 300 |
| Low temperature stability | ++ | ++ | ± | + | + | ++ |

TABLE 9

| (The first agent) | Comparative Example 17 | Comparative Example 18 | Comparative Example 19 | Comparative Example 20 |
|---|---|---|---|---|
| Triethanolammonium polyoxyethylene (2) alkyl (12,14) ether sulfate | — | — | 10 | — |
| Triethanolammonium behenyl ether sulfate | 5 | — | — | — |
| Polyoxyethylene (2) oleyl ether | 5 | — | 5 | 5 |
| Polyoxyethylene (5) octylphenyl ether | — | — | — | 5 |
| Undecyl-N-hydroxy-N-carboxymethylimidazolinium betaine | — | 5 | 2 | — |
| Cocoyl Amide Propyldimethyl Glycine | — | 5 | 8 | — |
| Sodium Lauroamphoacetate | | | | |
| Oleic acid | 5 | 3 | 3 | 4 |
| Isostearic acid (Emery #871 desalted product) | — | — | — | — |
| Isopropanol | — | — | 5 | 8 |
| Monoethanolamine | 1 | 1 | 2 | 2 |
| Ammonia water (28%) | 10 | 10 | 10 | 1 |
| L-ascorbic acid | 0.5 | 0.5 | 0.5 | 0.5 |
| Paraphenyl enediamine | 1.0 | 1.0 | 1.0 | 1.0 |
| Resorcinol | — | 1.0 | 1.0 | 1.0 |
| Purified water | to 100 | to 100 | to 100 | to 100 |
| Weight ratio (anionic surface active agent/amphoteric surface active agent) | 10/0 | 0/10 | 5/5 | 6/4 |
| pH at the time of mixing | 9.0 | 9.1 | 8.9 | 7.9 |
| Dyeability | + | — | ± | − |
| Dryness to the touch | + | ++ | − | − |
| Viscosity after mixing | 300 | 300 | 1000 | 1200 |
| Low temperature stability | − | + | ± | − |

| (The first agent) | Comparative Example 21 | Comparative Example 22 | Comparative Example 23 | Comparative Example 24 |
|---|---|---|---|---|
| Triethanolammonium polyoxyethylene (2) alkyl (12,14) ether sulfate | — | — | 10 | 12 |
| Triethanolammonium behenyl ether sulfate | — | 10 | — | — |
| Polyoxyethylene (2) oleyl ether | 5 | — | — | — |
| Polyoxyethylene (5) octylphenyl ether | 5 | — | — | — |
| Undecyl-N-hydroxy-N-carboxymethyl imidazolinium betaine | 10 | — | — | 4 |
| Cocoyl Amide Propyldimethyl Glycine | — | — | — | 4 |
| Sodium Lauroamphoacetate | — | — | — | — |
| Oleic acid | 3 | 3 | — | — |
| Isostearic acid (Emery #871 desalted product) | — | — | — | — |
| Isopropanol | — | — | — | — |
| Monoethanolamine | 1 | 2 | 2 | 2 |
| Ammonia water (28%) | 5 | 10 | 8 | 9 |
| L-ascorbic acid | 0.5 | 0.5 | 0.5 | 0.5 |
| Paraphenylenediamine | 1.0 | 1.0 | 1.0 | 1.0 |
| Resorcinol | 1.0 | — | 1.0 | 1.0 |
| Purified water | to 100 | to 100 | to 100 | to 100 |
| Weight ratio (anionic surface active agent/amphoteric surface active agent) | 0/10 | 10/0 | 10/0 | 6/4 |
| pH at the time of mixing | 8.3 | 9.3 | 9.2 | 8.8 |
| Dyeability | ± | ± | + | + |
| Dryness to the touch | ± | ++ | + | + |
| Viscosity after mixing | 1700 | 180 | 120 | 1100 |
| Low temperature stability | ± | + | + | − |

As apparent from the above Tables 5 to 9, the hair dyes of the invention are excellent in dyeability, and free from dryness to the touch, and for example, when they are prepared as the first agent and the second agent, they are low in viscosity, respectively, moderate in the viscosity after mixing and moreover excellent in low temperature stability. Further, in all of the hair dyes of the invention, good thickening effect was ascertained, all of them exhibited viscosities of 500 cps or more, and it is seen that they have high thickening effect.

Example 40 and Comparative Example 25 (Usual System)

In the following example, the effects of the composition of the invention wherein two or more of amphoteric surface active agents or semipolar surface active agents are used in combination are illustrated.

The following first agent and the second agent of the invention or a usual system were mixed in a ratio of 1:1 to prepare a hair dye, and using hair strands, the difference in dyeability between the invention and the usual system was evaluated based on relations between time for which the hair strands were left alone and the L value.

Further, the viscosities of the first agent and the second agent, and the viscosity after mixing of both were measured.

|  | (weight %) |
|---|---|
| [The first agent] (Example 40) |  |
| Sodium polyoxyethylene (1.5) alkyl (12, 14) ether sulfate | 10.0 |
| Undecyl-N-hydroxyethyl-N-carboxymethylimidazolinium betaine | 3.0 |
| Cocoyl Amide Propyldimethyl Glycine | 7.0 |
| Oleic acid | 3.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Perfume | Appropriate amount |
| Purified water | Balance |
| Total | 100.0 |
| [The first agent] (Comparative example 25) |  |
| Polyoxyethylene (2) oleyl ether | 15.0 |
| Polyoxyethylene (5) octylphenyl ether | 5.0 |
| Oleic acid | 10.0 |
| Monoethanolamine | 2.0 |
| Ammonia water (28%) | 10.0 |
| Paraphenylenediamine | 1.0 |
| Resorcinol | 1.0 |
| L-ascorbic acid | 0.5 |
| Sodium hydrosulfite | 0.1 |
| Perfume | Appropriate amount |
| Purified water | Balance |
| Total | 100.0 |

|  | (weight %) |
|---|---|
| [The second agent] |  |
| Aqueous hydrogen peroxide (30%) | 20.0 |
| Methyl paraben | Appropriate amount |
| EDTA | Appropriate amount |
| Phosphate buffer | Adjusted to pH 3 |
| Purified water | Balance |
| Total | 100.0 |

The L value at 20 minutes after the treatment with the hair dye of Example 40 was 14.3 and that in the case of the comparative example was 17.8, and also by visual observation, the product of the invention was found to be superior to the usual system in dyeability.

Next, the dyed hair was irradiated with carbon arc for 20 hours or with a xenon lamp for 30 hours, and change of L values (ΔL) was checked. In Comparative example 25, ΔL was 12.0 (xenon), whereas in Example 40, ΔL was 4.2 (xenon), and the hair dyed with the present example was found to be slow to discolor.

Further, as to the first agent of Example 40, the pH was 10.85 and the viscosity was 260 cps, and as to the second agent, the pH was 2.1 and the viscosity was 8 cps, and after both were mixed, the pH became 9.3 and the viscosity became 6,500 cps, and remarkable thickening effect was observed.

Next, the first agent and the second agent of Example 40 were used, and an appropriate amount of a pH-adjusting agent (ammonia water or phosphoric acid) was added at the time of mixing to prepare hair dyes of pH 5, 6 and 12, respectively. When viscosity was measured, the viscosities of these hair dyes were 480 cps, 1,220 cps and 1,030 cps, respectively, and it was found that in the hair dyes of the invention wherein the pH is 6 to 12, excellent thickening effect can be obtained. Further, the L values at 20 minutes after the hair dyeing treatment were 50, 25 and 36, respectively, and it was revealed that dyeability is high in the range of pH 6 to 12.

Examples 41 to 56 and Comparative Examples 26 to 35

Evaluation was made according to the abovementioned evaluation method on hair dyes obtained by mixing the first agents having various compositions with the second agent used in Example 40. The results are shown together in Tables 10 to 14.

Comparative examples herein referred to are examples of the invention except for Comparative example 32, but they were classified as comparative examples in view of comparison with specific combination use of amphoteric surface active agents or semipolar surface active agents.

TABLE 10

| (The first agent) | Example 41 | Example 42 | Example 43 | Example 44 | Example 45 | Example 46 |
|---|---|---|---|---|---|---|
| Triethanolammonium polyoxyethylene (2) alkyl (12,14) ether sulfate | 8 | 10 | 15 | 10 | 10 | 10 |
| Polyoxyethylene (2) oleyl ether |  |  |  |  |  |  |
| Polyoxyethylene (5) octylphenyl ether | — | — | — | — | — | — |
| Undecyl-N-hydroxy-N-carboxymethylimidazolinium betaine | 2 | 1 | 2 | 3 | 4 | 4 |

TABLE 10-continued

| (The first agent) | Example 41 | Example 42 | Example 43 | Example 44 | Example 45 | Example 46 |
|---|---|---|---|---|---|---|
| Cocoyl Amide Propyldimethyl Glycine | 6 | 9 | 8 | 12 | 6 | 6 |
| Sodium Lauroamphoacetate | — | — | — | — | — | — |
| Oleic acid | 2 | 3 | 3 | 4 | 3 | 3 |
| Isostearic acid (Emery #871 desalted product) | — | — | — | — | — | — |
| Isopropanol | — | — | — | — | — | — |
| Monoethanolamine | 1 | 2 | 2 | 2 | 1 | 1 |
| Ammonia water (28%) | 10 | 10 | 10 | 10 | 10 | 15 |
| L-ascorbic acid | 0.5 | 0.5 | 0.5 | 0.5 | 0.5 | 0.5 |
| Paraphenyl enediamine | 1.0 | 1.0 | 1.0 | 1.0 | 1.0 | 1.0 |
| Resorcinol | — | 1.0 | 1.0 | 1.0 | 1.0 | 1.0 |
| Purified water | to 100 | to 100 | to 100 | to 100 | to 100 | to 100 |
| Weight ratio (anionic surface active agent/amphoteric surface active agent) | 5/5 | 5/5 | 6/4 | 4/6 | 5/5 | 5/5 |
| pH at the time of mixing | 9.5 | 9.3 | 9.2 | 8.9 | 9.3 | 9.6 |
| Dyeability | ++ | ++ | ++ | ++ | ++ | ++ |
| Dryness to the touch | ++ | ++ | ++ | ++ | ++ | ++ |
| Viscosity after mixing | 3000 | 5500 | 7000 | 5500 | 6000 | 700 |
| Low temperature stability | ++ | ++ | ++ | ++ | ++ | ++ |

TABLE 11

| (The first agent) | Example 47 | Example 48 | Example 49 | Example 50 | Example 51 |
|---|---|---|---|---|---|
| Triethanolammonium polyoxyethylene (2) alkyl (12,14) ether sulfate | 10 | 10 | 10 | 10 | 10 |
| Polyoxyethylene (2) oleyl ether | — | — | — | — | — |
| Polyoxyethylene (5) octylphenyl ether | — | — | — | — | — |
| Undecyl-N-hydroxy-N-carboxymethylimidazolinium betaine | 2 | 2 | 3 | 5 | 8 |
| Cocoyl Amide Propyldimethyl Glycine | — | 2 | 4 | — | 1 |
| Sodium Lauroamphoacetate | 8 | 6 | 3 | 5 | 1 |
| Oleic acid | 2 | 2 | 3 | 3 | 2 |
| Isostearic acid (Emery #871 desalted product) | — | 1 | 1 | — | 1 |
| Isopropanol | — | — | — | — | — |
| Monoethanolamine | 1 | 1 | 2 | 2 | 1 |
| Ammonia water (28%) | 10 | 10 | 10 | 10 | 10 |
| L-ascorbic acid | 0.5 | 0.5 | 0.5 | 0.5 | 0.5 |
| Paraphenyl enediamine | 1.0 | 1.0 | 1.0 | 1.0 | 1.0 |
| Resorcinol | — | 1.0 | 1.0 | 1.0 | 1.0 |
| Purified water | to 100 | to 100 | to 100 | to 100 | to 100 |
| Weight ratio (anionic surface active agent/amphoteric surface active agent) | 5/5 | 5/5 | 5/5 | 5/5 | 5/5 |
| pH at the time of mixing | 9.4 | 9.2 | 8.9 | 9.3 | 9.2 |
| Dyeability | ++ | ++ | ++ | ++ | ++ |
| Dryness to the touch | ++ | ++ | ++ | ++ | ++ |
| Viscosity after mixing | 7000 | 8500 | 6500 | 5500 | 6000 |
| Low temperature stability | ++ | ++ | ++ | ++ | ++ |

TABLE 12

| (The first agent) | Example 52 | Example 53 | Example 54 | Example 55 | Example 56 |
|---|---|---|---|---|---|
| Triethanolammonium polyoxyethylene (2) alkyl (12,14) ether sulfate | 12 | 12 | 10 | 10 | 10 |
| Undecyl-N-hydroxy-N-carboxymethylimidazolinium betaine | 8 | 8 | 7 | 7 | 7 |
| Cocoyl Amide Propyldimethyl Glycine | 4 | 4 | 2 | 2 | 2 |
| Coconut oil fatty acid amidopropyl-N,N-dimethyl-N-sulfopropyl betaine | — | — | 1 | — | — |
| Lauroyl-N,N-dimethyl-N-sulfopropyl betaine | — | — | — | 1 | — |
| Lauryldimethylamine oxide | — | — | — | — | 1 |
| Oleic acid | 3 | 3 | 2 | 2 | 2 |
| Isostearic acid (Emery #871 desalted product) | — | — | 1 | 1 | 1 |
| Isopropanol | 1.5 | 3.0 | — | — | — |
| Monoethanolamine | 2 | 2 | 1 | 1 | 1 |
| Ammonia water (28%) | 10 | 10 | 10 | 10 | 10 |
| L-ascorbic acid | 0.5 | 0.5 | 0.5 | 0.5 | 0.5 |
| Paraphenyl enediamine | 1.0 | 1.0 | — | — | — |
| Resorcinol | 0.2 | 0.2 | 1.0 | 1.0 | 1.0 |
| Purified water | to 100 | to 100 | to 100 | to 100 | to 100 |

TABLE 12-continued

| (The first agent) | Example 52 | Example 53 | Example 54 | Example 55 | Example 56 |
|---|---|---|---|---|---|
| Weight ratio (anionic surface active agent/amphoteric surface active agent) | 5/5 | 5/5 | 5/5 | 5/5 | 5/5 |
| pH at the time of mixing | 9.0 | 9.1 | 9.1 | 9.2 | 9.2 |
| Dyeability | ++ | ++ | ++ | ++ | ++ |
| Dryness to the touch | + | + | ++ | ++ | ++ |
| Viscosity after mixing | 3000 | 3000 | 4500 | 4700 | 3800 |
| Low temperature stability | ++ | ++ | ++ | ++ | ++ |

TABLE 13

| (The first agent) | Comparative Example 26 | Comparative Example 27 | Comparative Example 28 | Comparative Example 29 | Comparative Example 30 | Comparative Example 31 |
|---|---|---|---|---|---|---|
| Triethanolammonium polyoxyethylene (2) alkyi (12, 14) ether sulfate | 6 | 6 | 6 | 0 | 3 | 12 |
| Polyoxyethylene (2) oleyl ether | — | — | — | — | — | — |
| Polyoxyethylene (5) octylphenyl ether | — | — | — | — | 5 | — |
| Undecyl-N-hydroxy-N-carboxymethylimidazolinium betaine | 14 | — | 6 | 10 | 7 | 8 |
| Cocoyl Amide Propyldimethyl Glycine | — | 14 | 8 | — | — | 4 |
| Sodium Lauroamphoacetate | — | — | — | — | — | — |
| Oleic acid | 2 | 3 | 3 | 4 | 3 | 3 |
| Isostearic acid (Emery #871 desalted product) | — | — | — | — | — | — |
| Isopropanol | — | — | 5 | 4 | — | 4 |
| Monoethanolamine | 1 | 1 | 2 | 2 | 1 | 2 |
| Ammonia water (28%) | 10 | 10 | 10 | 10 | 10 | 10 |
| L-ascorbic acid | 0.5 | 0.5 | 0.5 | 0.5 | 0.5 | |
| Paraphenyl enediamine | 1.0 | 1.0 | 1.0 | 1.0 | 1.0 | 1.0 |
| Resorcinol | — | 1.0 | 1.0 | 1.0 | 1.0 | 0.2 |
| Purified water | to 100 | to 100 | to 100 | to 100 | to 100 | |
| Weight ratio (anionic surface active agent/amphoteric surface active agent) | 3/7 | 3/7 | 3/7 | 0/10 | 3/7 | 5/5 |
| pH at the time of mixing | 9.4 | 9.5 | 9.0 | 8.9 | 9.2 | 9.1 |
| Dyeability | ++ | ++ | ++ | ++ | + | ++ |
| Dryness to the touch | ++ | ++ | ± | ± | ± | ± |
| Viscosity after mixing | 200 | 300 | 250 | 1000 | 1200 | 400 |
| Low temperature stability | ++ | ++ | ± | − | ± | ++ |

TABLE 14

| (The first agent) | Comparative Example 32 | Comparative Example 33 | Comparative Example 34 | Comparative Example 35 |
|---|---|---|---|---|
| Triethanolammonium polyoxyethylene (2) alkyl (12,14) ether sulfate | 10 | — | — | 8 |
| Polyoxyethylene (2) oleyl ether | 5 | — | 5 | — |
| Polyoxyethylene (5) octylphenyl ether | — | — | 5 | — |
| Undecyl-N-hydroxy-N-carboxymethylimidazolinium betaine | — | 5 | 10 | 2 |
| Cocoyl Amide Propyldimethyl Glycine | — | 5 | — | 6 |
| Sodium Lauroamphoacetate | — | — | — | — |
| Oleic acid | — | 3 | 3 | — |
| Isostearic acid (Emery #871 desalted product) | — | — | — | — |
| Isopropanol | — | — | — | — |
| Monoethanolamine | 1 | 1 | 1 | 1 |
| Ammonia water (28%) | 10 | 10 | 10 | 10 |
| L-ascorbic acid | 0.5 | 0.5 | 0.5 | 0.5 |
| Paraphenyl enediamine | 1.0 | 1.0 | 1.0 | 1.0 |
| Resorcinol | — | 1.0 | 1.0 | — |
| Purified water | to 100 | to 100 | to 100 | to 100 |
| Weight ratio (anionic surface active agent/amphoteric surface active agent) | — | — | — | 5/5 |
| pH at the time of mixing | 9.8 | 9.8 | 9.3 | 9.8 |
| Dyeability | + | ± | ± | ++ |
| Dryness to the touch | — | ++ | ± | + |
| Viscosity after mixing | 110 | 200 | 1400 | 1200 |
| Low temperature stability | ± | + | ± | ± |

As apparent from the above Tables 10 to 14, the hair dyes of the invention are excellent in dyeability, and free from dryness to the touch, moderate in the viscosity after mixing and moreover excellent in low temperature stability. Further, in all of the hair dyes of the invention, good thickening effect was ascertained, and particularly, as to hair dyes containing an imidazolinium betaine-type surface active agent together with an amidobetaine-type, amidosulfobetaine-type, betaine-type or sulfobetaine-type surface active agent or a tertiary amine oxide-type semipolar surface active agent as the amphoteric surface active agent and/or the semipolar surface active agent, all of them exhibited viscosities of 500 cps or more, and it is seen that they have high thickening effect.

Example 57 and Comparative Examples 36 and 37 (Usual System)

The effects of the composition of the invention wherein a cationic polymer is used as an additional component is illustrated.

The following first agent and the second agent of the invention or a usual system were mixed in a ratio of 1:1 to prepare a hair dye, and using hair strands, the difference in dyeability between the invention and the usual system was evaluated based on relations between time for which the hair strands were left alone and the L value.

Further, the viscosities of the first agent and the second agent, and the viscosity after mixing of both were measured.

|  | (weight %) |
|---|---|
| [The first agent] (Prescription 1-A) | |
| Sodium polyoxyethylene (1.5) alkyl (12, 14) ether sulfate | 10.0 |
| Undecyl-N-hydroxyethyl-N-carboxymethylimidazolinium betaine | 5.0 |
| Cocoyl Amide Propyldimethyl Glycine | 5.0 |
| Oleic acid | 3.0 |
| Propylene glycol | 5.0 |
| Monoethanolamine | 2.0 |
| Ammonia water (28%) | 10.0 |
| [The first agent] (Prescription 1-B) | |
| Polyoxyethylene (3) oleyl ether | 15.0 |
| Polyoxyethylene (4) octylphenyl ether | 5.0 |
| Ethanol | 10.0 |
| Monoethanolamine | 2.0 |
| Ammonia water (28%) | 5.0 |
| Paraphenylenediamine | 2.0 |
| Purified water | Balance |
| Total | 100.0 |
| [The second agent] (Prescription 2-A) | |
| Aqueous hydrogen peroxide (30%) | 20.0 |
| Methyl paraben | 0.1 |
| Sodium stannate | 0.1 |
| O-[2-hydroxy-3-(trimethyl ammoniapropyl] hydroxycellulose chloride [Polymer JR-400 (produced by Union Carbide Co.)] | 1.0 |
| Phosphate buffer | Adjusted to pH 2 |
| Purified water | Balance |
| Total | 100.0 |
| [The second agent] (Prescription 2-B) | |
| Aqueous hydrogen peroxide (30%) | 20.0 |
| Methylparaben | 0.1 |

-continued

|  | (weight %) |
|---|---|
| Sodium stannate | 0.1 |
| Phosphate buffer | Adjusted to pH 2 |
| Purified water | Balance |
| Total | 100.0 |

|  | Example 57 | Comparative example 36 | Comparative example 37 |
|---|---|---|---|
| The first agent | Prescription 1-A | Prescription 1-B | Prescription 1-A |
| The second agent | Prescription 2-A | Prescription 2-B | Prescription 2-B |
| Viscosity of the first agent | 150 | 70 | 150 |
| Viscosity of the second agent | 40 | 40 | 15 |
| Viscosity at the time of mixing | 2,800 | 2,500 | 450 |
| Dyeability | ++ | ± | ++ |
| Dryness to the touch | ++ | − | ++ |
| Low temperature stability | ++ | + | ++ |

The L value at 20 minutes after the treatment with Example 57 was 12.9 and that in the case of Comparative example 36 was 16.1, and also by visual observation, the product of the invention was found to be superior to the usual system in dyeability.

Further, as to the first agent of Example 57, the pH was 11.2 and the viscosity was 150 cps, and as to the second agent, the pH was 2.0 and the viscosity was 40 cps, and after both were mixed, the pH became 9.5 and the viscosity became 2,800 cps, and remarkable thickening effect was observed.

Next, the first agent and the second agent of Example 57 were used, and an appropriate amount of a pH-adjusting agent (ammonia water or phosphoric acid) was added at the time of mixing to prepare hair dyes of pH 5, 6 and 12, respectively. When viscosity was measured, the viscosities of these hair dyes were 300 cps, 1,500 cps and 650 cps, respectively, and it was found that in the hair dyes of the invention wherein the pH is 6 to 12, excellent thickening effect can be obtained. Further, the L values at 20 minutes after the hair dyeing treatment were 24.0, 12.0 and 15.2, respectively, and it was revealed that dyeability is high in the range of pH 6 to 12.

Examples 58 to 81 and Comparative Examples 38 to 45

Evaluation was made according to the above-mentioned evaluation method on hair dyes obtained by mixing the first agents having various compositions with the second agents having various compositions shown in Table 15 to Table 18. All of the pH values of the hair dyes in Tables 15 to 17 were 6 to 12.

TABLE 15

|  | Example 58 | Example 59 | Example 60 | Example 61 | Example 62 | Example 63 | Example 64 | Example 65 |
|---|---|---|---|---|---|---|---|---|
| (The first agent) | | | | | | | | |
| Triethanolammonium polyoxyethylene (2) alkyl (12, 14) ether sulfate | 8 | 10 | 15 | 10 | 10 | 10 | 10 | 8 |
| Sodium α-alkenyl (12,13) sulfonate | — | — | — | — | — | — | — | — |
| Sodium lauroylmethyltaurate | — | — | — | — | — | — | — | — |
| Undecyl-N-hydroxy-N-carboxy-methylimidazolinium betaine | 8 | — | 2 | 3 | 4 | 3 | 5 | 4 |
| Cocoyl Amide Propyldimethyl Glycine | — | — | 8 | 12 | — | 7 | 5 | 8 |
| Sodium Lauroamphoacetate | — | — | — | — | 6 | — | — | — |
| Oleic acid | 2 | 3 | 3 | 3 | 3 | 3 | 4 | — |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 10 | 15 | 10 | 15 | 10 | 15 | 15 | 10 |
| L-ascorbic acid | 0.5 | 0.5 | 0.5 | 0.5 | 0.5 | 0.5 | 0.5 | 0.5 |
| Sodium hydrosulfite | — | 0.1 | — | — | 0.1 | — | 0.1 | — |
| Paraphenylenediamine | 1 | 1 | 0.5 | 1 | 1 | 1 | 1.5 | 0.8 |
| Resorcinol | — | 1 | 0.2 | 0.5 | 0.5 | 1 | 0.8 | 0.4 |
| Purified water | to 100 | to 100 | to 100 | to 100 | to 100 | to 100 | to 100 | to 100 |
| (The second agent) | | | | | | | | |
| O-[2-hydroxy-3-(trimethylammonio)-propyl]hydroxyethylcellulose chloride | 0.1 | 0.5 | — | — | — | 0.5 | 0.2 | — |
| Dimethylmethylenepiperidinium polychloride | — | — | 0.5 | — | — | — | — | 0.2 |
| Dimethylallyammonium chloride-acrylamide copolymer | — | — | — | 0.5 | — | — | — | — |
| Vinylpyrrolidone-N,N-dimethylaminoethyl methacrylate-stearyl acrylate-tripropylene glycol diacrylate copolymer | — | — | — | — | 0.5 | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methyl paraben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/2 | 1.5/1 |
| Weight ratio (anionic surface active agent/amphoteric surface active agent) | 5/5 | 10/0 | 6/4 | 4/6 | 5/5 | 5/5 | 5/5 | 4/6 |
| pH at the time of mixing | 9.5 | 9.8 | 9.2 | 9.5 | 9.2 | 9.2 | 9 | 9.4 |
| Dyeability | ++ | ++ | ++ | ++ | ++ | ++ | ++ | ++ |
| Dryness to the touch | ++ | ++ | ++ | ++ | ++ | ++ | ++ | ++ |
| Viscosity of the first agent | 100 | 120 | 110 | 150 | 130 | 130 | 150 | 110 |
| Viscosity of the second agent | 10 | 10 | 10 | 5 | 15 | 16 | 10 | 10 |
| Viscosity after mixing | 3200 | 1500 | 4000 | 2500 | 1600 | 1200 | 800 | 1500 |
| Low temperature stability | ++ | ++ | ++ | ++ | ++ | ++ | ++ | ++ |

TABLE 16

|  | Example 66 | Example 67 | Example 68 | Example 69 | Example 70 | Example 71 | Example 72 | Example 73 |
|---|---|---|---|---|---|---|---|---|
| (The first agent) | | | | | | | | |
| Triethanolammonium polyoxyethylene (2) alkyl (12,14) ether sulfate | 8 | 10 | 10 | — | — | — | 5 | 5 |
| Sodium α-alkenyl (12,13) sulfonate | — | — | 2 | 8 | 8 | 15 | — | 3 |
| Sodium lauroylmethyltaurate | — | — | — | — | — | — | 5 | 13 |
| Undecyl-N-hydroxy-N-carboxy-methylimidazolinium betaine | 2 | 1 | 2 | 2 | 2 | 5 | 4 | 6 |
| Cocoyl Amide Propyldimethyl Glycine | 6 | 9 | 6 | 4 | 10 | 10 | 6 | 6 |
| Sodium Lauroamphoacetate | — | — | — | 2 | — | — | — | — |
| Oleic acid | 2 | 3 | 3 | 3 | 3 | 3 | 3 | 2 |
| Isostearic acid (Emery #871 desalted product) | — | — | — | — | — | — | — | 1 |

TABLE 16-continued

|  | Example 66 | Example 67 | Example 68 | Example 69 | Example 70 | Example 71 | Example 72 | Example 73 |
|---|---|---|---|---|---|---|---|---|
| Monoethanolamine | 1 | 2 | 2 | 2 | 2 | 2 | 2.5 | 3 |
| Ammonia water (28%) | 10 | 10 | 10 | 10 | 12 | 10 | — | — |
| L-ascorbic acid | 0.5 | 0.5 | 0.5 | 0.5 | 0.5 | 0.5 | 0.5 | 0.5 |
| Paraphenylenediamine | 1 | 1 | 0.5 | 1 | 1 | 1 | 1 | 1 |
| Resorcinol | — | 1 | 1 | 1 | 1 | 1 | 0.5 | 1 |
| 1,3-Butylene glycol | 2 | 1 | 3 | 2 | 1.5 | 2 | 4.5 | 4 |
| Ethanol | — | — | — | — | — | 2 | — | — |
| Purified water | to 100 | to 100 | to 100 | to 100 | to 100 | to 100 | to 100 | to 100 |
| (The second agent) |  |  |  |  |  |  |  |  |
| O-[2-hydroxy-3-(trimethylammonio)-propyl]hydroxyethylcellulose chloride | — | 0.1 | 0.5 | — | 0.1 | — | — | 2 |
| Dimethylmethylenepiperidinium polychloride | 0.5 | — | — | — | — | 0.5 | — | — |
| Dimethylallyammonium chloride acrylamide copolymer | — | — | — | — | 0.3 | 0.1 | — | — |
| Vinyl pyrrolidone-N,N-dimethylaminoethyl methacrylate-stearyl acrylate-tripropylene glycol diacrylate copolymer | — | — | — | — | — | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methyl paraben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/1 | 1/1 |
| Weight ratio (anionic surface active agent/amphoteric surface active agent) | 5/5 | 5/5 | 6/4 | 5/5 | 6/4 | 5/5 | 5/5 | 6/4 |
| pH at the time of mixing | 9.5 | 9.3 | 9.2 | 9.3 | 9.5 | 9.5 | 7.5 | 7.8 |
| Dyeability | ++ | ++ | ++ | ++ | ++ | ++ | ++ | ++ |
| Dryness to the touch | ++ | ++ | ++ | ++ | ++ | ++ | ++ | ++ |
| Viscosity of the first agent | 100 | 120 | 110 | 80 | 130 | 110 | 120 | 150 |
| Viscosity of the second agent | 10 | 10 | 10 | 10 | 5 | 10 | 15 | 10 |
| Viscosity after mixing | 2000 | 4500 | 4500 | 1800 | 2500 | 1700 | 800 | 1200 |
| Low temperature stability | ++ | ++ | ++ | ++ | ++ | ++ | ++ | ++ |

TABLE 17

|  | Example 74 | Example 75 | Example 76 | Example 77 | Example 78 | Example 79 | Example 80 | Example 81 |
|---|---|---|---|---|---|---|---|---|
| (The first agent) |  |  |  |  |  |  |  |  |
| Triethanolammonium polyoxyethylene (2) alkyl (12,14) ether sulfate | 2 | — | 8 | 4 | 1 | 6 | — | 5 |
| Sodium α-alkenyl (12,13) sulfonate | 8 | 18 | 2 | 12 | 4 | — | 10 | 5 |
| Sodium lauroylmethyltaurate | — | — | — | — | — | 4 | — | — |
| Undecyl-N-hydroxy-N-carboxy-methylimidazolinium betaine | 2 | 2 | 2 | 2 | 1 | 5 | 5 | 2 |
| Cocoyl Amide Propyldimethyl Glycine | 6 | — | 8 | 2 | 4 | 2 | 5 | 8 |
| Sodium Lauroamphoacetate | — | — | — | — | — | 3 | — | — |
| Oleic acid | 3 | 3 | 3 | 3 | 3 | 3 | 3 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 15 | 10 | 5 | 10 | 10 | 10 | 11 | 6 |
| L-ascorbic acid | 0.5 | 0.5 | 0.5 | 0.5 | 0.5 | 0.5 | 0.5 | 0.5 |
| Paraphenylenediamine | 1 | 1 | 1 | 1 | 0.5 | 1 | 0.5 | 1 |
| Resorcinol | 0.5 | 1 | 1 | 0.5 | 1 | 1 | 1 | 1 |
| 1,3-Butylene glycol | 1 | 0.5 | 3 | 1 | 0.5 | 2 | 0.5 | 2.5 |
| Ethanol | — | — | — | — | — | — | — | 0.5 |
| Purified water | to 100 | to 100 | to 100 | to 100 | to 100 | to 100 | to 100 | to 100 |
| (The second agent) |  |  |  |  |  |  |  |  |
| O-[2-hydroxy-3-(trimethylammonio)-propyl]hydroxyethylcellulose chloride | 0.5 | 4 | 5 | 2 | 0.01 | 0.2 | 0.5 | 0.5 |

TABLE 17-continued

|  | Example 74 | Example 75 | Example 76 | Example 77 | Example 78 | Example 79 | Example 80 | Example 81 |
|---|---|---|---|---|---|---|---|---|
| Dimethylmethylenepiperidinium polychloride | — | — | — | — | — | — | — | — |
| Dimethylallyammonium chloride-acrylamide copolymer | — | — | — | — | — | — | — | 0.1 |
| Vinylpyrrolidone-N,N-dimethylaminoethyl methacrylate-stearyl acrylate-tripropylene glycol diacrylate copolymer | — | — | — | — | — | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1.5 | 1/1 |
| Weight ratio (anionic surface active agent/amphoteric surface active agent) | 5/5 | 9/1 | 6/4 | 8/2 | 5/5 | 5/5 | 5/5 | 5/5 |
| pH at the time of mixing | 11.5 | 9.3 | 8.3 | 9.4 | 9.2 | 9.3 | 9.4 | 9 |
| Dyeability | ++ | ++ | ++ | ++ | ++ | ++ | ++ | ++ |
| Dryness to the touch | + | ++ | ++ | ++ | ++ | ++ | ++ | ++ |
| Viscosity of the first agent | 90 | 60 | 120 | 80 | 70 | 100 | 180 | 120 |
| Viscosity of the second agent | 30 | 40 | 45 | 35 | 20 | 30 | 110 | 40 |
| Viscosity after mixing | 1800 | 1500 | 4200 | 5100 | 1600 | 2100 | 4100 | 1500 |
| Low temperature stability | ++ | ++ | ++ | ++ | ++ | ++ | ++ | ++ |

TABLE 18

|  | Comparative Example 38 | Comparative Example 39 | Comparative Example 40 | Comparative Example 41 | Comparative Example 42 | Comparative Example 43 | Comparative Example 44 | Comparative Example 45 |
|---|---|---|---|---|---|---|---|---|
| (The first agent) | | | | | | | | |
| Triethanolammonium polyoxyethylene (2) alkyl (12,14) ether sulfate | 6 | 6 | 3 | 10 | — | — | 8 | 5 |
| Sodium α-alkenyl (12,13) sulfonate | — | — | — | — | — | 3 | — | — |
| Sodium lauroylmethyltaurate | — | — | — | — | — | — | — | — |
| Undecyl-N-hydroxy-N-carboxymethylimidazolinium betaine | 14 | — | 7 | — | 5 | 10 | 2 | 6 |
| Cocoyl Amide Propyldimethyl Glycine | — | 14 | — | — | 5 | — | 6 | 6 |
| Sodium Lauroamphoacetate | — | — | — | — | — | — | — | — |
| Oleic acid | 2 | 3 | 3 | — | 3 | 3 | — | 2 |
| Polyoxyethylene (2) oleyl ether | — | — | 5 | 5 | — | 5 | — | — |
| Polyoxyethylene (5) octylphenyl ether | — | — | — | — | — | 5 | — | — |
| Sodium alkylbenzenesulfonate | — | — | — | — | — | — | — | 5 |
| Isostearic acid (Emery #871 desalted product) | — | — | — | — | — | — | — | — |
| Monoethanolamine | 1 | 2 | 2 | 2 | 2 | 2 | 2 | 3 |
| Ammonia water (28%) | 10 | 10 | 10 | 10 | 12 | 10 | 10 | 10 |
| L-ascorbic acid | 0.5 | 0.5 | 0.5 | 0.5 | 0.5 | 0.5 | 0.5 | 0.5 |
| Paraphenylenediamine | 1 | 1 | 0.5 | 1 | 1 | 1 | 1 | 1 |
| Resorcinol | 1 | 1 | 1 | 1 | 1 | 0.5 | 1 | 1 |
| 1,3-Butylene glycol | — | — | — | — | — | — | — | — |
| Ethanol | — | — | — | — | — | — | 10 | 10 |
| Isopropanol | 8 | — | — | — | — | — | 8 | — |
| Purified water | to 100 | to 100 | to 100 | to 100 | to 100 | to 100 | to 100 | to 100 |
| (The second agent) | | | | | | | | |
| O-[2-hydroxy-3-(trimethylammonio)-propyl]hydroxyethylcellulose chloride | 0.5 | 0.5 | — | 0.2 | 0.5 | — | 0.2 | 0.2 |
| Dimethylmethylenepiperidinium polychloride | — | — | 0.5 | — | — | 0.5 | — | — |

TABLE 18-continued

|  | Comparative Example 38 | Comparative Example 39 | Comparative Example 40 | Comparative Example 41 | Comparative Example 42 | Comparative Example 43 | Comparative Example 44 | Comparative Example 45 |
|---|---|---|---|---|---|---|---|---|
| Dimethylallyammonium chloride-acrylamide copolymer | — | — | — | — | — | — | — | — |
| Vinyl pyrrolidone-N N-dimethylaminoethyl methacrylate-stearyl acrylate-tripropylene glycol diacrylate copolymer | — | — | — | 0.1 | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1 | 1/1 |
| Weight ratio (anionic surface active agent/amphoteric surface active agent) | 3/7 | 3/7 | 3/7 | 10/0 | 0/10 | 0/10 | 5/5 | 4/6 |
| pH at the time of mixing | 9.4 | 9.5 | 9.2 | 9.8 | 9.8 | 9.3 | 9.8 | 9.8 |
| Dyeability | ++ | ++ | + | ± | ± | ± | ++ | + |
| Dryness to the touch | ++ | — | + | + | ++ | — | — | — |
| Viscosity of the first agent | 100 | 130 | 110 | 80 | 120 | 100 | 140 | 50 |
| Viscosity of the second agent | 40 | 40 | 30 | 30 | 20 | 30 | 20 | 20 |
| Viscosity after mixing | 200 | 300 | 1000 | 1500 | 200 | 1400 | 200 | 400 |
| Low temperature stability | ++ | ++ | ± | ± | + | ± | − | + |

From the results shown in Table 15 to Table 18, it is seen that the hair dyes of the invention each containing a cationic polymer as an additional component are also excellent in dyeability, free from dryness to the touch, low in viscosity on the first agent and the second agent, moderate in the viscosity after mixing and moreover excellent in low temperature stability. Further, in the usual hair dyes, for making the first agent low viscous and obtaining high viscosity at the time of mixing with the second agent, as shown in Comparative example 36, the nonionic surface active agent is compounded in a high concentration and the monohydric alcohol (isopropanol) is added so that the viscosity can be lowered, and heightened at the time of mixing, whereas in the invention, it is possible to make the first agent low viscous without incorporating a monohydric alcohol and attain high viscosity at the time of mixing.

Example 82 and Comparative Example 46 (Usual System)

In the following example, a further example is mentioned in the case where the composition of the invention is adjusted to pH 6 to 8.

The following first agent and the second agent of the invention or a usual system were mixed in a ratio of 3:1 to prepare a hair dye, and using hair strands, the difference in dyeability between the invention and the usual system was evaluated based on relations between time for which the hair strands were left alone and the L value.

Further, the viscosities of the first agent and the second agent, and the viscosity after mixing of both were measured.

|  | (weight %) |
|---|---|
| [The first agent] (Example 82) | |
| Sodium Polyoxyethylene (1.5) alkyl (12, 13) ether sulfate | 10.0 |
| Undecyl-N-hydroxyethyl-N-carboxymethylimidazolinium betaine | 10.0 |
| Oleic acid | 3.0 |
| Monoethanolamine | 2.0 |
| L-ascorbic acid | 0.5 |
| Paraphenylenediamine | 2.0 |
| Purified water | Balance |
| Total | 100.0 |
| [The first agent] (Comparative example 46) | |
| Polyoxyethylene (3) oleyl ether | 15.0 |
| Polyoxyethylene (4) octylphenyl ether | 5.0 |
| Benzyl alcohol | 20.0 |
| Monoethanolamine | 10.0 |
| L-ascorbic acid | 0.5 |
| Paraphenylenediamine | 2.0 |
| Purified water | Balance |
| Total | 100.0 |
| [The second agent] | |
| Aqueous hydrogen peroxide (30%) | 20.0 |
| Phosphoric acid | 0.2 |
| Disodium edetate | 0.2 |
| Purified water | Balance |
| Total | 100.0 |

The L value at 20 minutes after the treatment with Example 82 was 12.9 and that in the case of Comparative example was 16.1, and also by visual observation, the product of the invention was found to be superior to the usual system in dyeability.

Further, as to the first agent of Example 82, the pH was 9.5 and the viscosity was 10 cps, and as to the second agent, the pH was 1.5 and the viscosity was 8 cps, and after both were mixed, the pH became 7.2 and the viscosity became 5,000 cps, and thus it was found that the composition of the invention exhibits an enough viscosity not to drop from the hair.

Next, the first agent and the second agent of Example 82 were used, and an appropriate amount of a pH-adjusting agent (monoethanolamine or phosphoric acid) was added at the time of mixing to prepare hair dyes of pH 5, 6 and 8, respectively. When viscosity was measured, the viscosities of these hair dyes were 600 cps, 2,100 cps and 5,900 cps, respectively, and it was found that in the hair dyes of the invention wherein the pH is 6 to 8, excellent thickening effect can be obtained. Further, the L values at 20 minutes after the hair dyeing treatment were 21.0, 12.4 and 11.8, respectively, and it was revealed that dyeability is high in the range of pH 6 to 8.

Examples 83 to 88 and Comparative Examples 47 to 50

The first agents of the various compositions shown in Tables 19 and 20 and the second agent used in Example 82 (or Comparative example 46) were mixed in a ratio of 3:1 to 1:2 to prepare hair dyes, and using these hair dyes, evaluation was made according to the above-mentioned evaluation method. All the pH values of the hair dyes in Table 1 were 6 to 8. The results are shown together in Tables 19 and 20.

TABLE 19

| (The first agent) | Example 83 | Example 84 | Example 85 | Example 86 | Example 87 | Example 88 |
|---|---|---|---|---|---|---|
| Triethanolammonium polyoxyethylene (2) alkyl (12,14) ether sulfate | 8 | 10 | 10 | 12 | 8 | 6 |
| Polyoxyethylene (2) oleyl ether | — | — | — | — | — | — |
| Polyoxyethylene (8) octylphenyl ether | — | — | — | — | — | — |
| Undecyl-N-hydroxy-N-carboxymethylimidazolinium betaine | — | 10 | 10 | 8 | 12 | 14 |
| Sodium Lauroamphoacetate | 8 | — | — | — | — | — |
| Myristic acid | — | 2 | — | 1 | — | — |
| Isostearic acid (Emery #871 desalted product) | 2 | — | 3 | 2 | 3 | 3 |
| Isopropanol | | | | | | |
| Monoethanolamine | 1.0 | 1.0 | 1.0 | 1.0 | 1.0 | 1.0 |
| L-ascorbic acid | 0.5 | 0.5 | 0.5 | 0.5 | 0.5 | 0.5 |
| Paraphenylenediamine | 1 | 1 | 1 | 1 | 1 | 1 |
| Purified water | to 100 | to 100 | to 100 | to 100 | to 100 | to 100 |
| Weight ratio (anionic surface active agent/amphoteric surface active agent) | 5/5 | 5/5 | 5/5 | 6/4 | 4/6 | 3/7 |
| Dyeability | ++ | ++ | ++ | ++ | ++ | ++ |
| Dryness to the touch | ++ | ++ | ++ | ++ | ++ | + |
| Viscosity after mixing | ++ | ++ | ++ | ++ | ++ | ± |
| Low temperature stability | ++ | + | ++ | ++ | ++ | + |

TABLE 20

| (The first agent) | Comparative Example 47 | Comparative Example 48 | Comparative Example 49 | Comparative Example 50 |
|---|---|---|---|---|
| Triethanolammonium polyoxyethylene (2) alkyl (12,14) ether sulfate | — | 15 | — | — |
| Polyoxyethylene (2) oleyl ether | 15 | — | 30 | — |
| Polyoxyethylene (8) octylphenyl ether | 25 | — | — | — |
| Undecyl-N-hydroxy-N-carboxymethylimidazolinium betaine | — | — | — | 30 |
| Sodium Lauroamphoacetate | — | — | 10 | 2 |
| Myristic acid | — | 3 | — | — |
| Isostearic acid (Emery #871 desalted product) | 3 | — | 2 | — |
| Isopropanol | 10 | — | — | — |
| Monoethanolamine | 1.0 | 1.0 | 1.0 | 1.0 |
| L-ascorbic acid | 0.5 | 0.5 | 0.5 | 0.5 |
| Paraphenylenediamine | 1 | 1 | 1 | 1 |
| Purified water | to 100 | to 100 | to 100 | to 100 |
| Weight ratio (anionic surface active agent/amphoteric surface active agent) | — | — | — | — |
| Dyeability | + | ± | ± | ± |
| Dryness to the touch | − | − | − | − |
| Viscosity after mixing | + | − | − | − |
| Low temperature stability | − | − | + | ± |

From the results shown in Tables 19 to 20, it is seen that the hair dyes of the invention are excellent in dyeability, free from dryness to the touch, moderate in the viscosity after mixing and moreover excellent in low temperature stability. Further, in the usual hair dyes, for making the first agent low viscous and obtaining high viscosity at the time of mixing with the second agent, as shown in Comparative example 1, the nonionic surface active agent is compounded in a high concentration and the monohydric alcohol (isopropanol) is added so that the viscosity can be lowered, and heightened at the time of mixing, whereas in the invention, it is possible to make the first agent low viscous without incorporating a monohydric alcohol and attain high viscosity at the time of mixing.

Examples 89 to 107

Further compositions of the invention are shown below. When hair dyes were prepared using the first agent and the second agent of the compositions of Example 82, all the viscosities thereof were 500 cps or more, and it was ascertained that there were excellent effects in all of dyeability, dryness to the touch, fading properties, low temperature stability and usability.

Example 89

| (The first agent) | (weight %) |
|---|---|
| Undecyl-N-hydroxyethyl-N-carboxymethylimidazolinium betaine | 2.0 |
| Cocoyl Amide Propyldimethyl Glycine | 8.0 |
| Oleic acid | 3.0 |
| Keratin protein hydrolizate | 1.0 |
| Pyrrolidonecarboxylate salt | 1.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Metaaminophenol | 0.5 |
| Perfume | Appropriate amount |
| Purified water | Balance |
| Total | 100.0 |

| (The second agent) | |
|---|---|
| Sodium polyoxyethylene (1.5) alkyl (12, 14) ether sulfate | 10 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

Example 90

| (The first agent) | |
|---|---|
| Undecyl-N-hydroxyethyl-N-carboxymethylimidazolinium betaine | 8.0 |
| Cocoyl Amide Propyldimethyl Glycine | 7.0 |
| Myristic acid | 4.0 |
| Dimethyl polysiloxane 20 cs | 1.0 |
| Keratin hydrolizate | 1.0 |
| Monoethanolamine | 2.0 |
| Ammonia water (28%) | 10.0 |
| L-ascorbic acid | 0.5 |
| Sodium hydrosulfite | 0.2 |
| Paraphenylenediamine | 1.0 |
| Resorcinol | 0.5 |
| Metaaminophenol | 0.1 |

-continued

| | (weight %) |
|---|---|
| Perfume | Appropriate amount |
| Purified water | Balance |
| Total | 100.0 |

| (The second agent) | |
|---|---|
| Sodium α-alkenyl (12, 13) sulfonate | 8 |
| Sodium polyoxyethylene (1.5) alkyl (12, 14) ether sulfate | 2 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

Example 91

| (The first agent) | |
|---|---|
| Triethanolammonium polyoxyethylene (1.5) lauryl ether sulfate | 1.0 |
| Undecyl-N-hydroxyethyl-N-carboxymethylimidazolinium betaine | 5.0 |
| Sodium Lauroamphoacetate | 5.0 |
| Isostearic acid | 3.0 |
| Keratin protein hydrolizate | 1.0 |
| Dimethyl polysiloxane (polymerization degree 3,000 to 6,000) | 1.5 |
| Monoethanolamine | 2.0 |
| Ammonia water (28%) | 15.0 |
| L-Ascorbic acid | 0.5 |
| Thioglycolate salt | 1.0 |
| Paraphenylenediamine | 1.0 |
| Resorcinol | 0.5 |
| Orthoaminophenol | 1.0 |
| Perfume | Appropriate amount |
| Purified water | Balance |
| Total | 100.0 |

| (The second agent) | |
|---|---|
| Sodium α-alkenyl (12, 13) sulfonate | 10 |
| Carboxyvinyl polymer ("HivisWako 105", produced by Wako Pure Chemical Industries, Ltd.) | 0.5 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

Example 92

| (The first agent) | |
|---|---|
| Undecyl-N-hydroxyethyl-N-carboxymethylimidazolinium betaine | 2.0 |
| Cocoyl Amide Propyldimethyl Glycine | 8.0 |
| Oleic acid | 3.0 |
| 1,3-Butylene glycol | 3.0 |
| Collagen protein hydrolizate | 1.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Metaaminophenol | 0.5 |
| Perfume | Appropriate amount |
| Purified water | Balance |
| Total | 100.0 |

| (The second agent) | |
|---|---|
| Sodium polyoxyethylene (1.5) alkyl (12, 14) ether sulfate | 8 |
| Sodium lauroylmethyltaurate | 2 |

|   | (weight %) |
|---|---|
| O-[2-Hydroxy-3-(trimethylammonio)propyl]-hydroxyethylcellulose chloride | 0.5 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

Example 93

(The first agent)

|   | (weight %) |
|---|---|
| Undecyl-N-hydroxyethyl-N-carboxymethylimidazolinium betaine | 4.0 |
| Cocoyl Amide Propyldimethyl Glycine | 4.0 |
| Sodium Lauroamphoacetate | 4.0 |
| Isostearic acid | 3.0 |
| Keratin protein hydrolizate | 1.0 |
| Amino-modified silicone (produced by TORAY INDUSTRIES INC.; SM-8702C) | 3.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Paraaminophenol | 0.5 |
| Perfume | Appropriate amount |
| Purified water | Balance |
| Total | 100.0 |

(The second agent)

|   | (weight %) |
|---|---|
| Sodium α-alkenyl (12, 13) sulfonate | 12 |
| Sodium lauroylmethyltaurate | 8 |
| O-[2-Hydroxy-3-(trimethylammonio)propyl]-hydroxyethylcellulose chloride | 0.5 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

Example 94

(The first agent)

|   | (weight %) |
|---|---|
| Undecyl-N-hydroxyethyl-N-carboxymethylimidazolinium betaine | 5.0 |
| Cocoyl Amide Propyldimethyl Glycine | 3.0 |
| Oleic acid | 2.0 |
| Liquid paraffin | 2.0 |
| Glycerol | 4.0 |
| Dimethyl polysiloxane 100 cs | 1.0 |
| Sodium hydroxide | 1.0 |
| Ammonia water (28%) | 10.0 |
| L-ascorbic acid | 0.5 |
| Paraphenylenediamine | 1.0 |
| Resorcinol | 0.2 |
| Orthoaminophenol | 0.8 |
| Perfume | Appropriate amount |
| Purified water | Balance |
| Total | 100.0 |

(The second agent)

|   | (weight %) |
|---|---|
| Sodium polyoxyethylene (1.5) alkyl (12, 14) ether sulfate | 15 |
| Carboxyvinyl polymer ("HivisWako 105", produced by Wako Pure Chemical Industries, Ltd.) | 0.5 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

Example 95

(The first agent)

|   | (weight %) |
|---|---|
| Undecyl-N-hydroxyethyl-N-carboxymethylimidazolinium betaine | 1.0 |
| Cocoyl Amide Propyldimethyl Glycine | 8.0 |
| Isostearic acid | 3.0 |
| Quaternized collagen protein hydrolyzate | 1.5 |
| Myristic acid | 4.0 |
| Dimethyl polysiloxane 6 cs | 2.0 |
| Monoethanolamine | 4.0 |
| Ammonia water (28%) | 12.0 |
| L-ascorbic acid | 0.5 |
| Paraphenylenediamine | 0.5 |
| Resorcinol | 0.4 |
| Metaaminophenol | 0.3 |
| Paraaminoorthocresol | 0.2 |
| Perfume | Appropriate amount |
| Purified water | Balance |
| Total | 100.0 |

(The second agent)

|   | (weight %) |
|---|---|
| Sodium α-alkenyl (12, 13) sulfonate | 15 |
| Amino-modified silicone (Silicone SM-8702C, produced by TORAY INDUSTRIES INC.) | 1 |
| O-[2-Hydroxy-3-(trimethylammonio)propyl]-hydroxyethylcellulose chloride | 0.5 |
| Aqueous hydrogen peroxide (30%) | 20 |
| Methylparaben | Appropriate amount |
| Sodium stannate | Appropriate amount |
| Phosphate buffer | Adjusted to pH 3 |
| Purified water | Balance |
| Total | 100 |

In the following examples are shown examples of the first agents all of whose viscosities became 500 cps when used in combination with the second agent of Example 26 or 40, and which exhibited excellent properties in all of dyeability, dryness to the touch, fading properties, low temperature stability and usability.

Example 96

|   | (weight %) |
|---|---|
| Sodium polyoxyethylene (1.5) alkyl (12, 14) ether sulfate | 14.0 |
| Undecyl-N-hydroxyethyl-N-carboxymethylimidazolinium betaine | 2.0 |
| Cocoyl Amide Propyldimethyl Glycine | 4.0 |
| Oleic acid | 3.0 |
| Keratin protein hydrolyzate | 1.0 |
| Pyrrolidonecarboxylic acid salt | 1.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Metaaminophenol | 0.5 |
| Perfume | Appropriate amount |
| Purified water | Balance |
| Total | 100.0 |

Example 97

| | (weight %) |
|---|---|
| Sodium polyoxyethylene (1.5) alkyl (12, 14) ether sulfate | 15.0 |
| Undecyl-N-hydroxyethyl-N-carboxymethylimidazolinium betaine | 2.0 |
| Myristic acid | 4.0 |
| Dimethyl polysiloxane 20 cs | 1.0 |
| Keratin protein hydrolyzate | 1.0 |
| Monoethanolamine | 3.0 |
| L-ascorbic acid | 0.5 |
| Sodium hydrosulfite | 0.2 |
| Paraphenylenediamine | 1.0 |
| Resorcinol | 0.5 |
| Metaaminophenol | 0.1 |
| Perfume | Appropriate amount |
| Purified water | Balance |
| Total | 100.0 |

Example 98

| | (weight %) |
|---|---|
| Sodium polyoxyethylene (1.5) alkyl (12, 14) ether sulfate | 7.0 |
| Triethanolammonim polyoxyethylene (1.5) lauryl ether sulfate | 3.0 |
| Undecyl-N-hydroxyethyl-N-carboxymethylimidazolinium betaine | 2.0 |
| Sodium Lauroamphoacetate | 2.0 |
| Isostearic acid | 3.0 |
| Keratin protein hydrolyzate | 1.0 |
| Dimethyl polysiloxane (polymerization degree 3,000 to 6,000) | 1.5 |
| Monoethanolamine | 2.0 |
| Ammonia water (28%) | 15.0 |
| L-ascorbic acid | 0.5 |
| Thioglycolate salt | 1.0 |
| Paraphenylenediamine | 1.0 |
| Resorcinol | 0.5 |
| Orthoaminophenol | 1.0 |
| Perfume | Appropriate amount |
| Purified water | Balance |
| Total | 100.0 |

Example 99

| | (weight %) |
|---|---|
| Sodium polyoxyethylene (1.5) alkyl (12, 14) ether sulfate | 18.0 |
| Undecyl-N-hydroxyethyl-N-carboxymethylimidazolinium betaine | 2.0 |
| Cocoyl Amide Propyldimethyl Glycine | 1.0 |
| Oleic acid | 3.0 |
| 1,3-Butylene glycol | 3.0 |
| Collagen protein hydrolyzate | 1.0 |
| Monoethanolamine | 2.0 |
| Ammonia water (28%) | 5.0 |
| L-ascorbic acid | 0.5 |
| Paraphenylenediamine | 1.0 |
| Resorcinol | 1.0 |
| Metaaminophenol | 0.5 |
| Perfume | Appropriate amount |
| Purified water | Balance |
| Total | 100.0 |

Example 100

| | (weight %) |
|---|---|
| Sodium polyoxyethylene (1.5) alkyl (12, 14) ether sulfate | 25.0 |
| Undecyl-N-hydroxyethyl-N-carboxymethylimidazolinium betaine | 1.0 |
| Cocoyl Amide Propyldimethyl Glycine | 1.0 |
| Sodium Lauroamphoacetate | 1.0 |
| Isostearic acid | 3.0 |
| Keratin protein hydrolyzate | 1.0 |
| Amino-modified silicone (SM-8702C; produced by TORAY INDUSTRIES INC.) | 3.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Paraaminophenol | 0.5 |
| Perfume | Appropriate amount |
| Purified water | Balance |
| Total | 100.0 |

Example 101

| | (weight %) |
|---|---|
| Sodium polyoxyethylene (1.5) alkyl (12, 14) ether sulfate | 25.0 |
| Oleic acid | 2.0 |
| Liquid paraffin | 2.0 |
| Glycerol | 4.0 |
| Dimethyl polysiloxane 100 cs | 1.0 |
| Sodium hydroxide | 1.0 |
| Ammonia water (28%) | 10.0 |
| L-ascorbic acid | 0.5 |
| Paraphenylenediamine | 1.0 |
| Resorcinol | 0.2 |
| Orthoaminophenol | 0.8 |
| Perfume | Appropriate amount |
| Purified water | Balance |
| Total | 100.0 |

Example 102

| | (weight %) |
|---|---|
| Sodium polyoxyethylene (1.5) alkyl (12, 14) etther sulfate | 20.0 |
| Undecyl-N-hydroxyethyl-N-carboxymethylimidazolinium betaine | 1.0 |
| Cocoyl Amide Propyldimethyl Glycine | 3.0 |
| Isostearic acid | 3.0 |
| Quaternized collagen protein hydrolyzate | 1.5 |
| Dimethyl polysiloxane 6 cs | 2.0 |
| Monoethanolamine | 4.0 |
| Ammonia water (28%) | 12.0 |
| L-ascorbic acid | 0.5 |
| Paraphenylenediamine | 0.5 |
| Resorcinol | 0.4 |
| Metaaminophenol | 0.3 |
| Paraaminoorthocresol | 0.2 |
| Perfume | Appropriate amount |
| Purified water | Balance |
| Total | 100.0 |

Example 103

| | (weight %) |
|---|---|
| Sodium polyoxyethylene (1.5) alkyl (12, 14) ether sulfate | 15.0 |
| Undecyl-N-hydroxyethyl-N-carboxymethylimidazolinium betaine | 8.0 |
| Cocoyl Amide Propyldimethyl Glycine | 7.0 |
| Myristic acid | 4.0 |
| Dimethyl polysiloxane 20 cs | 1.0 |
| Keratin hydrolyzate | 1.0 |
| Monoethanolamine | 4.0 |
| Ammonia water (28%) | 10.0 |
| L-ascorbic acid | 0.5 |
| Paraphenylenediamine | 1.0 |
| Resorcinol | 0.5 |
| Metaaminophenol | 0.1 |
| Perfume | Appropriate amount |
| Purified water | Balance |
| Total | 100.0 |

Example 104

| | (weight %) |
|---|---|
| Sodium polyoxyethylene (1.5) alkyl (12, 14) ether sulfate | 6.0 |
| Triethanolammonium polyoxyethylene (1.5) lauryl ether sulfate | 4.0 |
| Undecyl-N-hydroxyethyl-N-carboxymethylimidazolinium betaine | 5.0 |
| Sodium Lauroamphoacetate | 5.0 |
| Isostearic acid | 3.0 |
| Keratin protein hydrolyzate | 1.0 |

-continued

| | (weight %) |
|---|---|
| Dimethyl polysiloxane (polymerization degree 3,000 to 6,000) | 1.5 |
| Monoethanolamine | 2.0 |
| Ammonia water (28%) | 15.0 |
| L-ascorbic acid | 0.5 |
| Thioglycolate salt | 1.0 |
| Paraphenylenediamine | 1.0 |
| Resorcinol | 0.5 |
| Orhtoaminophenol | 1.0 |
| Perfume | Appropriate amount |
| Purified water | Balance |
| Total | 100.0 |

Example 105

| | |
|---|---|
| Sodium polyoxyethylene (1.5) alkyl (12, 14) ether sulfate | 5.0 |
| Sodium lauroylmethyltaurate | 5.0 |
| Undecyl-N-hydroxyethyl-N-carboxymethylimidazolinium betaine | 2.0 |
| Cocoyl Amide Propyldimethyl Glycine | 8.0 |
| Oleic acid | 3.0 |
| 1,3-Butylene glycol | 3.0 |
| Collagen protein hydrolyzate | 1.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Metaaminophenol | 0.5 |
| Perfume | Appropriate amount |
| Purified water | Balance |
| Total | 100.0 |

Example 106

| | |
|---|---|
| Sodium polyoxyethylene (1.5) alkyl (12, 14) ether sulfate | 8.0 |
| Undecyl-N-hydroxyethyl-N-carboxymethylimidazolinium betaine | 4.0 |
| Cocoyl Amide Propyldimethyl Glycine | 4.0 |
| Sodium Lauroamphoacetate | 4.0 |
| Isostearic acid | 3.0 |
| Keratin protein hydrolyzate | 1.0 |
| Amino-modified silicone (SM-8702C; produced by TORAY INDUSTRIES INC.) | 3.0 |
| Monoethanolamine | 2.0 |
| Ammonia water (28%) | 10.0 |
| L-ascorbic acid | 0.5 |
| Paraphenylenediamine | 1.0 |
| Resorcinol | 1.0 |
| Paraaminophenol | 0.5 |
| Perfume | Appropriate amount |
| Purified water | Balance |
| Total | 100.0 |

Example 107

| | |
|---|---|
| Sodium polyoxyethylene (1.5) alkyl (12, 14) ether sulfate | 12.0 |
| Undecyl-N-hydroxyethyl-N-carboxymethylimidazolinium betaine | 5.0 |
| Cocoyl Amide Propyldimethyl Glycine | 3.0 |
| Oleic acid | 2.0 |
| Liquid paraffin | 2.0 |
| Glycerol | 2.0 |
| Dimethyl polysiloxane 100 cs | 1.0 |
| Sodium hydroxide | 1.0 |
| Ammonia water (28%) | 10.0 |
| L-ascorbic acid | 0.5 |
| Paraphenylenediamine | 1.0 |
| Resorcinol | 0.2 |
| Orthoaminophenol | 0.8 |
| Perfume | Appropriate amount |
| Purified water | Balance |
| Total | 100.0 |

In the following examples, hair-bleaching agent (decoloring agent) compositions of the invention are specifically described in comparison with comparative examples.

Evaluation of the compositions of the invention was conducted according to the following criteria.

1) Decolorization effect test using hair strands Untreated hair strands (2 g) were coated with 10 g of a decoloring agent, and evaluation was made from the relations between time for which the hair strans were left alone and the L value. The L value means the value of L in the color difference equation of Hunter.

2) Comparative test on decolorization effect and dryness to the touch by a panel of experts A series of decolorization operations was conducted, and decolorization effect of the hair of the head and dryness to the touch after drying were evaluated according to the following criterion, using a panel of 10 experts.

<Decolorization effect>

++ ... Decolorization effect is remarkably good and the hair is uniformly decolorized + ... Decolorization effect is good and the hair is uniformly decolorized ± ... Decolorization effect is a little poor − ... The hair is unevenly decolorized and decolorization effect is low <Dryness to the touch>

++ ... The hair is not dry to the touch and gives smooth touch

+ ... The hair is not dry to the touch

± ... The hair is a little dry to the touch

− ... The hair is remarkably dry to the touch

3) Viscosity of mixed solution

The first agent and the second agent were mixed and the viscosity of the mixed solution was measured at 30° C. using a Brook-field type viscometer.

4) Low temperature stability

The first agent (100 g) was stored in a constant temperature bath of −5° C. for one month, and the state thereof was visually observed and evaluated according to the following criterion.

++ ... Any change is not observed at all compared with the initial state

+ ... Any change is not observed at all compared with the initial state, but there is a slight increase of the viscosity ± ... A slight turbidity is formed − ... Separation occurs Example 108 and Comparative Example 51 (Usual System)

The following first agent and the second agent of the invention or a usual system were mixed in a ratio of 1:1 to prepare a hair-bleaching agent, and using black hair strands, the difference in decolorization effect between the invention and the usual system was evaluated based on relations between time for which the black hair strands were left alone and the L value, according to the above-mentioned method.

Further, the viscosities of the first agent and the second agent, and the viscosity after mixing of both were measured.

| | (weight %) |
|---|---|
| Example 108 | |
| (The first agent) | |
| Undecyl-N-hydroxyethyl-N-carboxymethylimidazolinium betaine | 3.0 |
| Cocoyl Amide Propyldimethyl Glycine | 7.0 |
| Oleic acid | 3.0 |
| Monoethanolamine | 2.0 |
| Ammonia water (28%) | 10.0 |
| Perfume | Appropriate amount |
| Purified water | Balance |
| Total | 100.0 |
| (The second agent) | |
| Sodium Polyoxyethylene (1.5) alkyl (12, 14) ether sulfate | 10.0 |
| Aqueous hydrogen peroxide | 20.0 |
| Methylparaben | Appropriate amount |
| Sodium stannate | Appropriate amount |
| Phosphate buffer | Adjusted to pH 3 |
| Purified water | Balance |
| Total | 100.0 |
| Comparative example 51 | |
| (The first agent) | |
| Polyoxyethylene (2) oleyl ether | 15.0 |
| Polyoxyethylene (5) octylphenyl ether | 5.0 |
| Oleic acid | 10.0 |
| Monoethanolamine | 2.0 |
| Ammonia water (28%) | 10.0 |
| Perfume | Appropriate amount |
| Purified water | Balance |
| Total | 100.0 |
| (The second agent) | |
| Aqueous hydrogen peroxide (30%) | 20.0 |
| Methylparaben | Appropriate amount |
| Sodium stannate | Appropriate amount |
| Phosphate buffer | Adjusted to pH 3 |
| Purified water | Balance |
| Total | 100.0 |

As to the first agent of Example 108, the pH was 10.58 and the viscosity was 120 cps, and as to the second agent, the pH was 3.0 and the viscosity was 12 cps, and after both were mixed, the pH became 9.2 and the viscosity became 3,800 cps, and remarkable thickening effect was observed.

Next, the first agent and the second agent of Example 108 were used, and an appropriate amount of a pH-adjusting agent (ammonia water or phosphoric acid) was added at the time of mixing to prepare decoloring agents of pH 5, 6 and 12, respectively. When viscosity was measured, the viscosities of these decoloring agents were 480 cps, 3,020 cps and 1,050 cps, respectively, and it was found that in the decoloring agents wherein the pH was made to be 6 to 12, excellent thickening effect can be obtained. Further, the ΔL values at 20 minutes after the decolorization treatment were 5, 18 and 32, respectively, and it was revealed that decolorization effect is high in the range of pH 6 to 12.

Example 109 and Comparative examples 52 and 53
(Usual System)

The following first agent and the second agent of the invention or a usual system were mixed in a ratio of 1:1 to prepare a hair-bleaching agent, and using black hair strands, the difference in decolorization effect between the invention and the usual system was evaluated based on relations between time for which the black hair strands were left alone and the L value.

Further, the viscosities of the first agent and the second agent, and the viscosity after mixing of both were measured.

| | (weight %) |
|---|---|
| [The first agent] (Prescription 1-A) | |
| Sodium Polyoxyethylene (1.5) alkyl (12, 14) ether sulfate | 10.0 |
| Undecyl-N-hydroxyethyl-N-carboxymethylimidazolinium betaine | 5.0 |
| Cocoyl Amide Propyldimethyl Glycine | 5.0 |
| Oleic acid | 3.0 |
| Propylene glycol | 5.0 |
| Monoethanolamine | 2.0 |
| Ammonia water (28%) | 10.0 |
| Purified water | Balance |
| Total | 100.0 |
| [The first agent] (Prescription 1-B) | |
| Polyoxyethylene (3) oleyl ether | 15.0 |
| Polyoxyethylene (4) octylphenyl ether | 5.0 |
| Ethanol | 10.0 |
| Monoethanolamine | 2.0 |
| Ammonia water (28%) | 5.0 |
| Purified water | Balance |
| Total | 100.0 |
| [The second agent] (Prescription 2-A) | |
| Aqueous hydrogen peroxide (30%) | 20.0 |
| Methylparaben | 0.1 |
| Sodium stannate | 0.1 |
| O-[2-hydroxy-3-(trimethylammoniapropyl]-hydroxycellulose [Polymer JR-400 (produced by Union Carbide Co.)] | 1.0 |
| Phosphate buffer | Adjusted to pH 2 |
| Purified water | Balance |
| Total | 100.0 |
| [The second agent] (Prescription 2-B) | |
| Aqueous hydrogen peroxide (30%) | 20.0 |
| Methylparaben | 0.1 |
| Sodium stannate | 0.1 |
| Phosphate buffer | Adjusted to pH 2 |
| Purified water | Balance |
| Total | 100.0 |

| | Example 109 | Comparative example 52 | Comparative example 53 |
|---|---|---|---|
| The first agent | Prescription 1-A | Prescription 1-B | Prescription 1-A |
| The second agent | Prescription 2-A | Prescription 2-B | Prescription 2-B |
| Viscosity of the first agent | 170 | 70 | 170 |
| Viscosity of the second agent | 40 | 40 | 15 |
| Viscosity at the time of mixing | 3,200 | 2,500 | 460 |
| Dyeability | ++ | ± | ++ |
| Dryness to the touch | ++ | − | ++ |
| Low temperature stability | ++ | + | ++ |

As to the first agent of Example 109, the pH was 11.0 and the viscosity was 170 cps, and as to the second agent, the pH was 2.0 and the viscosity was 40 cps, and after both were mixed, the pH became 9.4 and the viscosity became 3,200 cps, and remarkable thickening effect was observed.

Next, the first agent and the second agent of Example 109 were used, and an appropriate amount of a pH-adjusting agent (ammonia water or phosphoric acid) was added at the time of mixing to prepare hair-bleaching agents of pH 5, 6 and 12, respectively. When viscosity was measured, the viscosities of these hairbleaching agents were 330 cps, 1,600 cps and 800 cps, respectively, and it was found that in the hair-bleaching agents wherein the pH was made to be 6 to 12, excellent thickening effect can be obtained. Further, the ΔL values at 20 minutes after the decolorization treatment were 4, 18 and 30, respectively, and it was revealed that decolorization effect is high in the range of pH 6 to 12.

Examples 110 to 157 and Comparative Examples 54 to 69

The first agents and the second agents of various compositions shown in Table 21 to Table 28 were mixed to prepare hair-bleaching agents, respectively, and these hair-bleaching agents were evaluated according to the above-mentioned evaluation methods. All the pH values of the hair-bleaching agents in Table 1 to Table 3 were 6 to 12.

TABLE 21

|  | Example 110 | Example 111 | Example 112 | Example 113 | Example 114 | Example 115 | Example 116 | Example 117 |
|---|---|---|---|---|---|---|---|---|
| (The first agent) | | | | | | | | |
| Undecyl-N-hydroxy-N-carboxy-methylimidazolinium betaine | 8 | — | 2 | 3 | 4 | 8 | 15 | 4 |
| Cocoyl Amide Propyldimethyl Glycine | — | — | 8 | 12 | — | 7 | 3 | 2.66 |
| Sodium Lauroamphoacetate | — | — | — | — | 6 | — | — | — |
| Oleic acid | 2 | 3 | 3 | 3 | 3 | 3 | 4 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 10 | 15 | 10 | 15 | 10 | 15 | 15 | 10 |
| Purified water | to 100 | to 100 | to 100 | to 100 | to 100 | to 100 | to 100 | to 100 |
| (The second agent) | | | | | | | | |
| Triethanolammonium polyoxyethylene (2) alkyl (12,14) ether sulfate | 8 | 10 | 15 | 10 | 10 | 10 | 9 | 15 |
| Sodium α-alkenyl (12,13) sulfonate | — | — | — | — | — | — | — | — |
| Sodium lauroylmethyltaurate | — | — | — | — | — | — | — | — |
| O-[2-hydroxy-3-(trimethylammonio)-propyl]hydroxyethylcellulose chloride | — | — | — | — | — | — | — | — |
| Dimethylmethylenepiperidinium polychloride | — | — | — | — | — | — | — | — |
| Dimethylallyammonium chloride acrylamide copolymer | — | — | — | — | — | — | — | — |
| Vinyl pyrrolidone-N,N—dimethylaminoethyl methacrylate—stearyl acrylate-tripropylene glycol diacrylate copolymer | — | — | — | — | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/2 | 1.5/1 |
| Weight ratio (anionic surface active agent/amphoteric surface active agent) | 5/5 | 10/0 | 6/4 | 4/6 | 5/5 | 5/5 | 5/5 | 4/6 |
| pH at the time of mixing | 9.4 | 9.8 | 9 | 9.4 | 9.1 | 9.1 | 8.9 | 9.4 |
| Decolorization effect | ++ | ++ | ++ | ++ | ++ | ++ | + | ++ |
| Dryness to the touch | ++ | ++ | ++ | ++ | ++ | ++ | ++ | ++ |
| Viscosity of the first agent | 120 | 140 | 120 | 180 | 140 | 140 | 170 | 130 |
| Viscosity of the second agent | 40 | 40 | 40 | 55 | 45 | 50 | 45 | 40 |
| Viscosity after mixing | 3500 | 3500 | 5500 | 2900 | 4200 | 2200 | 2600 | 1900 |
| Low temperature stability | ++ | ++ | ++ | ++ | ++ | ++ | ++ | ++ |

TABLE 22

|  | Example 115 | Example 119 | Example 120 | Example 121 | Example 122 | Example 123 | Example 124 | Example 125 |
|---|---|---|---|---|---|---|---|---|
| (The first agent) | | | | | | | | |
| Undecyl-N-hydroxy-N-carboxy-methylimidazolinium betaine | 2 | 1 | 2 | 2 | 2 | 5 | 4 | 6 |
| Cocoyl Amide Propyldimethyl Glycine | 6 | 9 | 6 | 4 | 10 | 10 | 6 | 6 |

TABLE 22-continued

|  | Example 115 | Example 119 | Example 120 | Example 121 | Example 122 | Example 123 | Example 124 | Example 125 |
|---|---|---|---|---|---|---|---|---|
| Sodium Lauroamphoacetate | — | — | — | 2 | — | — | — | — |
| Oleic acid | 2 | 3 | 3 | 3 | 3 | 3 | 3 | 2 |
| Isostearic acid (Emery #871 desalted product) | — | — | — | — | — | — | — | 1 |
| Monoethanolamine | 1 | 2 | 2 | 2 | 2 | 2 | 7.0 | 6.0 |
| Ammonia water (28%) | 10 | 10 | 10 | 10 | 12 | 10 | — | — |
| 1,3-Butylene Glycol | 2 | 1 | 3 | 2 | 1.5 | 2 | 4.5 | 4 |
| Ethanol | — | — | — | — | — | 2 | — | — |
| Purified water | to 100 | to 100 | to 100 | to 100 | to 100 | to 100 | to 100 | to 100 |
| (The second agent) |  |  |  |  |  |  |  |  |
| Triethanolammonium polyoxyethylene (2) alkyl (12,14) ether sulfate | 8 | 10 | 10 | — | — | — | 5 | 5 |
| Sodium α-alkenyl (12,13) sulfonate | — | — | 2 | 8 | 8 | 10 | — | 3 |
| Sodium lauroylmethyltaurate | — | — | — | — | — | — | 5 | — |
| O-[2-hydroxy-3-(trimethylammonio)-propyl]hydroxyethylcellulose chloride | — | — | 0.5 | — | — | — | — | — |
| Dimethylmethylenepiperidinium polychloride | 0.5 | — | — | — | — | — | — | — |
| Dimethylallyammonium chloride acrylamide copolymer | — | — | — | 0.3 | — | — | — | — |
| Vinylpyrrolidone-N,N-dimethylaminoethyl methacrylate-stearyl acrylate-tripropylene glycol diacrylate copolymer | — | — | — | — | — | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/1 | 1/1 |
| Weight ratio (anionic surface active agent/amphoteric surface active agent) | 5/5 | 5/5 | 6/4 | 5/5 | 6/4 | 5/5 | 5/5 | 6/4 |
| pH at the time of mixing | 9.4 | 9.3 | 9.1 | 9.2 | 9.4 | 9.3 | 9.1 | 8.9 |
| Decolorization effect | ++ | ++ | ++ | ++ | ++ | ++ | + | + |
| Dryness to the touch | ++ | ++ | ++ | ++ | ++ | ++ | ++ | ++ |
| Viscosity of the first agent | 120 | 140 | 140 | 90 | 150 | 120 | 160 | 180 |
| Viscosity of the second agent | 40 | 40 | 40 | 30 | 40 | 30 | 40 | 40 |
| Viscosity after mixing | 3500 | 5800 | 7200 | 4600 | 4400 | 2800 | 3800 | 4800 |
| Low temperature stability | ++ | ++ | ++ | ++ | ++ | ++ | ++ | ++ |

TABLE 23

|  | Example 126 | Example 127 | Example 128 | Example 129 | Example 130 | Example 131 | Example 132 | Example 133 |
|---|---|---|---|---|---|---|---|---|
| (The first agent) |  |  |  |  |  |  |  |  |
| Undecyl-N-hydroxy-N-carboxymethylimidazolinium betaine | 2 | 2 | 2 | 2 | 1 | 5 | 5 | 2 |
| Cocoyl Amide Propyldimethyl Glycine | 6 | — | 8 | 2 | 4 | 2 | 11 | 8 |
| Sodium Lauroamphoacetate | — | — | — | — | — | 3 | — | — |
| Oleic acid | 3 | 3 | 3 | 3 | 3 | 3 | 3 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 15 | 10 | 8 | 10 | 10 | 10 | 11 | 6 |
| 1,3-Butylene glycol | 1 | 0.5 | 3 | 1 | 0.5 | 2 | 0.5 | 2.5 |
| Ethanol | — | — | — | — | — | — | — | 0.5 |
| Purified water | to 100 | to 100 | to 100 | to 100 | to 100 | to 100 | to 100 | to 100 |
| (The second agent) |  |  |  |  |  |  |  |  |
| Triethanolammonium polyoxyethylene (2) alkyl (12,14) ether sulfate | 2 | — | 8 | 4 | 1 | 6 | — | 5 |
| Sodium α-alkenyl (12,13) sulfonate | 8 | 18 | 2 | 12 | 4 | — | 10 | 5 |
| Sodium lauroylmethyltaurate | — | — | — | — | — | 4 | — | — |

TABLE 23-continued

|  | Example 126 | Example 127 | Example 128 | Example 129 | Example 130 | Example 131 | Example 132 | Example 133 |
|---|---|---|---|---|---|---|---|---|
| O-[2-hydroxy-3-(trimethylammonio)-propyl]hydroxyethylcellulose chloride | — | — | — | — | — | — | — | — |
| Dimethylmethylenepiperidinium polychloride | — | — | — | — | — | — | — | — |
| Dimethylallyammonium chloride-acrylamide copolymer | — | — | — | — | — | — | — | — |
| Vinyl pyrrolidone-N,N-dimethylaminoethyl methacrylate-stearyl acrylate-tripropylene glycol diacrylate copolymer | — | — | — | — | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1.5 | 1/1 |
| Weight ratio (anionic surface active agent/amphoteric surface active agent) | 5/5 | 9/1 | 6/4 | 8/2 | 5/5 | 5/5 | 5/5 | 5/5 |
| pH at the time of mixing | 11.4 | 9.1 | 8.8 | 9.3 | 9.1 | 9.1 | 9.4 | 8.9 |
| Decolorization effect | ++ | ++ | + | ++ | ++ | ++ | ++ | ++ |
| Dryness to the touch | + | ++ | ++ | ++ | ++ | ++ | ++ | ++ |
| Viscosity of the first agent | 100 | 80 | 160 | 90 | 90 | 110 | 190 | 150 |
| Viscosity of the second agent | 30 | 40 | 45 | 35 | 20 | 30 | 40 | 40 |
| Viscosity after mixing | 1500 | 3700 | 6200 | 3000 | 650 | 900 | 4600 | 5900 |
| Low temperature stability | ++ | ++ | ++ | ++ | ++ | ++ | ++ | ++ |

TABLE 24

|  | Example 134 | Example 135 | Example 136 | Example 137 | Example 138 | Example 139 | Example 140 | Example 141 |
|---|---|---|---|---|---|---|---|---|
| (The first agent) | | | | | | | | |
| Triethanolammonium polyoxyethylene (2) alkyl (12,14) ether sulfate | 8 | 10 | 15 | 10 | 10 | 10 | 10 | 8 |
| Sodium α-alkenyl (12,13) sulfonate | — | — | — | — | — | — | — | — |
| Sodium lauroylmethyltaurate | — | — | — | — | — | — | — | — |
| Undecyl-N-hydroxy-N-carboxymethylimidazolinium betaine | 8 | — | 2 | 3 | 4 | 3 | 5 | 4 |
| Cocoyl Amide Propyldimethyl Glycine | — | — | 8 | 12 | — | 7 | 5 | 8 |
| Sodium Lauroamphoacetate | — | — | — | — | 6 | — | — | — |
| Oleic acid | 2 | 3 | 3 | 3 | 3 | 3 | 4 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 1 | 15 | 10 | 15 | 10 | 15 | 15 | 10 |
| Purified water | to 100 | to 100 | to 100 | to 100 | to 100 | to 100 | to 100 | to 100 |
| (The second agent) | | | | | | | | |
| O-[2-hydroxy-3-(trimethylammonio)-propyl]hydroxyethylcellulose chloride | 0.1 | 0.5 | — | — | — | 0.5 | 0.2 | — |
| Dimethylmethylenepiperidinium polychloride | — | — | 0.5 | — | — | — | — | — |
| Dimethylallyammonium chloride-acrylamide copolymer | — | — | — | 0.5 | — | — | — | 0.2 |
| Vinylpyrrolidone-N,N-dimethylaminoethyl methacrylate-stearyl acrylate-tripropylene glycol diacrylate copolymer | — | — | — | — | 0.5 | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |

TABLE 24-continued

|  | Example 134 | Example 135 | Example 136 | Example 137 | Example 138 | Example 139 | Example 140 | Example 141 |
|---|---|---|---|---|---|---|---|---|
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/2 | 1.5/1 |
| Weight ratio (anionic surface active agent/amphoteric surface active agent) | 5/5 | 10/0 | 6/4 | 4/6 | 5/5 | 5/5 | 5/5 | 4/6 |
| pH at the time of mixing | 9.5 | 9.8 | 9.2 | 9.5 | 9.2 | 9.2 | 9 | 9.4 |
| Decolorization effect | ++ | ++ | ++ | ++ | ++ | ++ | ++ | ++ |
| Dryness to the touch | ++ | ++ | ++ | ++ | ++ | ++ | ++ | ++ |
| Viscosity of the first agent | 150 | 130 | 140 | 160 | 160 | 140 | 150 | 120 |
| Viscosity of the second agent | 10 | 10 | 10 | 5 | 15 | 10 | 10 | 10 |
| Viscosity after mixing | 3500 | 1800 | 4500 | 2800 | 1700 | 1500 | 850 | 1700 |
| Low temperature stability | ++ | ++ | ++ | ++ | ++ | ++ | ++ | ++ |

TABLE 25

|  | Example 142 | Example 143 | Example 144 | Example 145 | Example 146 | Example 147 | Example 148 | Example 149 |
|---|---|---|---|---|---|---|---|---|
| (The first agent) | | | | | | | | |
| Triethanolammonium polyoxyethylene (2) alkyl (12,14) ether sulfate | 8 | 10 | 10 | — | — | — | 5 | 5 |
| Sodium α-alkenyl (12,13) sulfonate | — | — | 2 | 8 | 8 | 15 | — | 3 |
| Sodium lauroylmethyltaurate | — | — | — | — | — | — | 5 | — |
| Undecyl-N-hydroxy-N-carboxy-methylimidazolinium betaine | 2 | 1 | 2 | 2 | 2 | 5 | 4 | 6 |
| Cocoyl Amide Propyldimethyl Glycine | 6 | 9 | 6 | 4 | 10 | 10 | 6 | — |
| Sodium Lauroamphoacetate | — | — | — | 2 | — | — | — | — |
| Oleic acid | 2 | 3 | 3 | 3 | 3 | 3 | 3 | 2 |
| Isostearic acid (Emery #871 desalted product) | — | — | — | — | — | — | — | 1 |
| Monoethanolamine | 1 | 2 | 2 | 2 | 2 | 2 | 6.5 | 7.0 |
| Ammonia water (28%) | 10 | 10 | 10 | 10 | 12 | 10 | — | — |
| 1,3-Butylene glycol | 2 | 1 | 3 | 2 | 1.5 | 2 | 2.0 | 1.0 |
| Ethanol | — | — | — | — | — | 2 | — | — |
| Purified water | to 100 | to 100 | to 100 | to 100 | to 100 | to 100 | to 100 | to 100 |
| (The second agent) | | | | | | | | |
| O-[2-hydroxy-3-(trimethylammonio)-propyl]hydroxyethylcellulose chloride | — | 0.1 | 0.5 | — | 0.1 | — | — | 2 |
| Dimethylmethylenepiperidinium polychloride | 0.5 | — | — | — | — | 0.5 | — | — |
| Dimethylallyammonium chloride-acrylamide copolymer | — | — | — | 0.3 | 0.1 | — | — | — |
| Vinyl pyrrolidone-N,N-dimethylaminoethyl methacrylate-stearyl acrylate-tripropylene glycol diacrylate copolymer | — | — | — | — | — | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1.5 | 1/1 | 1/1 |
| Weight ratio (anionic surface active agent/amphoteric surface active agent) | 5/5 | 5/5 | 6/4 | 5/5 | 6/4 | 5/5 | 5/5 | 6/4 |
| pH at the time of mixing | 9.4 | 9.3 | 9.1 | 9.4 | 9.2 | 9.3 | 9.0 | 9.2 |

TABLE 25-continued

|  | Example 142 | Example 143 | Example 144 | Example 145 | Example 146 | Example 147 | Example 148 | Example 149 |
|---|---|---|---|---|---|---|---|---|
| Decolorization effect | ++ | ++ | ++ | ++ | ++ | ++ | ++ | ++ |
| Dryness to the touch | ++ | ++ | ++ | ++ | ++ | ++ | ++ | ++ |
| Viscosity of the first agent | 120 | 150 | 120 | 90 | 140 | 130 | 170 | 180 |
| Viscosity of the second agent | 10 | 10 | 10 | 10 | 5 | 10 | 15 | 10 |
| Viscosity after mixing | 2500 | 4800 | 4600 | 2000 | 2800 | 1800 | 750 | 1200 |
| Low temperature stability | ++ | ++ | ++ | ++ | ++ | ++ | ++ | ++ |

TABLE 26

|  | Example 150 | Example 151 | Example 152 | Example 153 | Example 154 | Example 155 | Example 156 | Example 157 |
|---|---|---|---|---|---|---|---|---|
| (The first agent) | | | | | | | | |
| Triethanolammonium polyoxyethylene (2) alkyl (12,14) ether sulfate | 2 | — | 8 | 4 | 1 | 6 | — | 5 |
| Sodium α-alkenyl (12,13) sulfonate | 8 | 18 | 2 | 12 | 4 | — | 10 | 5 |
| Sodium lauroylmethyltaurate | — | — | — | — | — | 4 | — | — |
| Undecyl-N-hydroxy-N-carboxy-methylimidazolinium betaine | 2 | 2 | 2 | 2 | 1 | 5 | 5 | 2 |
| Cocoyl Amide Propyldimethyl Glycine | 6 | — | 8 | 2 | 4 | 2 | 5 | 8 |
| Sodium Lauroamphoacetate | — | — | — | — | — | 3 | — | — |
| Oleic acid | 3 | 3 | 3 | 3 | 3 | 3 | 3 | 2 |
| Isostearic acid (Emery #871 desalted product) | — | — | — | — | — | — | — | — |
| Monoethanolamine | 1 | 2 | 2 | 2 | 2 | 2 | 2 | 1 |
| Ammonia water (28%) | 15 | 10 | 8 | 10 | 10 | 10 | 11 | 6 |
| 1,3-Butylene glycol | 1 | 0.5 | 3 | 1 | 0.5 | 2 | 0.5 | 2.5 |
| Ethanol | — | — | — | — | — | — | — | 0.5 |
| Purified water | to 100 | to 100 | to 100 | to 100 | to 100 | to 100 | to 100 | to 100 |
| (The second agent) | | | | | | | | |
| O-[2-hydroxy-3-(trimethylammonio)-propyl]hydroxyethylcellulose chloride | 0.5 | 4 | 5 | 2 | 0.01 | 0.2 | 0.5 | 0.5 |
| Dimethylmethylenepiperidinium polychloride | — | — | — | — | — | — | — | — |
| Dimethylallyammonium chloride-acrylamide copolymer | — | — | — | — | — | — | — | 0.1 |
| Vinyl pyrrolidone-N,N-dimethylaminoethyl methacrylate-stearyl acrylate-tripropylene glycol diacrylate copolymer | — | — | — | — | — | — | 0.5 | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1.5 | 1/1 |
| Weight ratio (anionic surface active agent/amphoteric surface active agent) | 5/5 | 9/1 | 6/4 | 8/2 | 5/5 | 5/5 | 5/5 | 5/5 |
| pH at the time of mixing | 11.4 | 9.1 | 8.8 | 9.3 | 9.2 | 9.1 | 9.3 | 9 |
| Decolorization effect | ++ | ++ | + | ++ | ++ | ++ | ++ | ++ |
| Dryness to the touch | + | ++ | ++ | ++ | ++ | ++ | ++ | ++ |
| Viscosity of the first agent | 90 | 60 | 60 | 80 | 70 | 100 | 180 | 120 |
| Viscosity of the second agent | 10 | 10 | 10 | 5 | 10 | 15 | 10 | |
| Viscosity after mixing | 1800 | 1500 | 2200 | 5100 | 1600 | 2100 | 4150 | 1500 |
| Low temperature stability | ++ | ++ | ++ | ++ | ++ | ++ | ++ | ++ |

TABLE 27

|  | Comparative Example 54 | Comparative Example 55 | Comparative Example 56 | Comparative Example 57 | Comparative Example 58 | Comparative Example 59 | Comparative Example 60 | Comparative Example 61 |
|---|---|---|---|---|---|---|---|---|
| (The first agent) | | | | | | | | |
| Undecyl-N-hydroxy-N-carboxymethylimidazolinium betaine | 14 | — | 7 | — | 5 | 10 | 2 | 6 |
| Cocoyl Amide Propyldimethyl Glycine | — | 14 | — | — | 5 | — | 6 | 6 |
| Sodium Lauroamphoacetate | — | 13 | — | — | — | — | — | — |
| Oleic acid | 2 | 3 | 3 | — | 3 | 3 | — | 2 |
| Sodium polyoxyethylene (1.5) alkyl (12,14) ether sulfate | — | | | | | | | |
| Polyoxyethylene (2) oleyl ether | — | | 5 | 5 | | 5 | | |
| Polyoxyethylene (5) octylphenyl ether | — | | | | | 5 | | |
| Sodium alkylbenzenesulfonate | — | | | | | | | 5 |
| Isostearic acid (Emery #871 desalted product) | — | — | — | — | — | — | 1 | |
| Monoethanolamine | 1 | 2 | 2 | 2 | 2 | 2 | 2 | 3 |
| Ammonia water (28%) | 10 | 10 | 10 | 10 | 12 | 10 | 10 | 10 |
| 1,3-Butylene glycol | — | — | — | | | | | |
| Ethanol | — | | | | | | | 10 |
| Isopropanol | 8 | | | | | | | |
| Purified water | to 100 | to 100 | to 100 | to 100 | to 100 | to 100 | to 100 | to 100 |
| (The second agent) | | | | | | | | |
| Triethanolammonium polyoxyethylene (2) alkyl (12,14) ether sulfate | 6 | 6 | 3 | 10 | — | — | 8 | 5 |
| Sodium α-alkenyl (12,13) sulfonate | — | — | — | — | — | — | — | 3 |
| Sodium lauroylmethyltaurate | — | — | — | — | — | — | — | — |
| O-[2-hydroxy-3-(trimethylammonio)propyl]hydroxyethylcellulose chloride | — | — | — | — | — | — | — | — |
| Dimethylmethylenepiperidinium polychloride | — | — | — | — | — | — | — | — |
| Dimethylallyammonium chloride-acrylamide copolymer | — | — | — | — | — | — | — | — |
| Vinylpyrrolidone-N,N-dimethylaminoethyl methacrylate-stearyl acrylate-tripropylene glycol diacrylate copolymer | — | — | — | — | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| mixing ratio (the first agent/the second agent) | 1/1 | 1/1 | 1/1 | 1/1 | 1/1 | 1/1 | 1/1 | 1/1 |
| Weight ratio (anionic surface active agent/amphoteric surface active agent) | 3/7 | 3/7 | 3/7 | 10/0 | 0/10 | 0/10 | 5/5 | 4/6 |
| pH at the time of mixing | 9.3 | 9.4 | 9.2 | 9.5 | 9.7 | 9.3 | 9.7 | 9.6 |
| Decolorization effect | ++ | ++ | ++ | ++ | ++ | ++ | ++ | ++ |
| Dryness to the touch | ++ | − | ± | ± | ++ | − | + | − |
| Viscosity of the first agent | 100 | 120 | 130 | 100 | 110 | 100 | 110 | 50 |
| Viscosity of the second agent | 60 | 90 | 40 | 30 | 20 | 20 | 20 | 30 |
| Viscosity after mixing | 250 | 400 | 1100 | 1400 | 250 | 1300 | 1400 | 420 |
| Low temperature stability | ++ | ++ | ± | ± | + | ± | − | + |

TABLE 28

|  | Comparative Example 62 | Comparative Example 63 | Comparative Example 64 | Comparative Example 65 | Comparative Example 66 | Comparative Example 67 | Comparative Example 68 | Comparative Example 69 |
|---|---|---|---|---|---|---|---|---|
| (The first agent) | | | | | | | | |
| Triethanolammonium polyoxyethylene (2) alkyl (12,14) ether sulfate | 6 | 6 | 3 | 10 | — | — | 8 | 5 |

TABLE 28-continued

|  | Comparative Example 62 | Comparative Example 63 | Comparative Example 64 | Comparative Example 65 | Comparative Example 66 | Comparative Example 67 | Comparative Example 68 | Comparative Example 69 |
|---|---|---|---|---|---|---|---|---|
| Sodium α-alkenyl (12,13) sulfonate | — | — |  |  |  |  | — | 3 |
| Sodium lauroylmethyltaurate | — | — | — | — | — | — | — | — |
| Undecyl-N-hydroxy-N-carboxy-methylimidazolinium betaine | 14 |  | 7 |  | 5 | 10 | 2 | 6 |
| Cocoyl Amide Propyldimethyl Glycine | — | 14 | — |  | 5 |  | 6 | 6 |
| Sodium Lauroamphoacetate | — | — | — |  | — | — | — | — |
| Oleic acid | 2 | 3 | 3 |  | 3 | 3 |  | 2 |
| Polyoxyethylene (2) oleyl ether | — |  | 5 | 5 |  | 5 |  |  |
| Polyoxyethylene (5) octylphenyl ether | — |  |  |  |  | 5 |  |  |
| sodium alkylbenzenesulfonate | — |  |  |  |  |  |  | 5 |
| Isostearic acid (Emery #871 desalted product) | — | — | — | — | — | — | — | 1 |
| Monoethanolamine | 1 | 2 | 2 | 2 | 2 | 2 | 2 | 3 |
| Ammonia water (28%) | 10 | 10 | 10 | 10 | 12 | 10 | 10 | 10 |
| 1,3-Butylene glycol | — | — | — |  |  |  |  |  |
| Ethanol |  |  |  |  |  |  |  | 10 |
| Isopropanol | 8 |  |  |  |  |  | 8 |  |
| Purified water | to 100 | to 100 | to 100 | to 100 | to 100 | to 100 | to 100 | to 100 |
| (The second agent) |  |  |  |  |  |  |  |  |
| O-[2-hydroxy-3-(trimethylammonio)-propyl]hydroxyethylcellulose chloride | 0.5 | 0.5 | — | 0.2 | 0.5 | — | 0.2 | 0.2 |
| Dimethylmethylenepiperidinium polychloride | — | — | 0.5 | — | — | 0.5 | — | — |
| Dimethylallyammonium chloride-acrylamide copolymer | — | — | — | — | — | — | — | — |
| Vinyl pyrrolidone-N,N-dimethylaminoethyl methacrylate-stearyl acrylate-tripropylene glycol diacrylate copolymer | — | — | — | 0.1 | — | — | — | — |
| Aqueous hydrogen peroxide (30%) | 20 | 20 | 20 | 20 | 20 | 20 | 20 | 20 |
| Sodium stannate | Appropriate amount | Appropriate amount | Appropriate amount | Appropriate amount | Appropriate amount | Appropriate amount | Appropriate amount | Appropriate amount |
| Methylparaben | Appropriate amount | Appropriate amount | Appropriate amount | Appropriate amount | Appropriate amount | Appropriate amount | Appropriate amount | Appropriate amount |
| Phosphate buffer | Adjusted to pH 3 | Adjusted to pH 3 | Adjusted to pH 3 | Adjusted to pH 3 | Adjusted to pH 3 | Adjusted to pH 3 | Adjusted to pH 3 | Adjusted to pH 3 |
| Purified water | to 100 | to 100 | to 100 | to 100 | to 100 | to 100 | to 100 | to 100 |
| Mixing ratio (the first agent/the second agent) | 1/1 | 1/1 | 1/1 | 1/1 | 1/1 | 1/1 | 1/1 | 1/1 |
| Weight ratio (anionic surface active agent/amphoteric surface active agent) | 3/7 | 3/7 | 3/7 | 10/0 | 0/10 | 0/10 | 5/5 | 4/6 |
| pH at the time of mixing | 9.3 | 9.4 | 9.2 | 9.6 | 9.7 | 9.1 | 9.6 | 9.5 |
| Decoloration effect | ++ | ++ | ++ | ++ | ++ | ++ | ++ | + |
| Dryness to the touch | ++ | − | ± | ± | ++ | − | − | − |
| Viscosity of the first agent | 150 | 140 | 110 | 80 | 130 | 100 | 150 | 50 |
| Viscosity of the second agent | 40 | 40 | 30 | 30 | 20 | 30 | 20 | 20 |
| Viscosity after mixing | 220 | 350 | 1000 | 1400 | 200 | 1500 | 250 | 400 |
| Low temperature stability | ++ | ++ | ± | ± | + | ± | − | + |

From the results shown in Table 21 to Table 28, it is seen that the hair-bleaching agents of the invention are excellent in decolorization effect, free from dryness to the touch, low in viscosity on the first agents and the second agents, moderate in the viscosity after mixing and moreover excellent in low temperature stability. Further, in the usual hair dyes, for making the first agent low viscous and obtaining high viscosity at the time of mixing with the second agent, as shown in Comparative example 52, the nonionic surface active agent is compounded in a high concentration and the monohydric alcohol (isopropanol) is added so that the viscosity can be lowered, and heightened at the time of mixing, whereas in the invention, it is possible to make the first agent low viscous without incorporating a monohydric alcohol and attain high viscosity at the time of mixing.

As further hair-bleaching agent compositions of the invention, there can be mentioned ones obtained by merely removing the dyes (compounds relating to the dyeing system) from the compositions of Examples 89 to 107 or substituting alkalinizing agents for the dyes. Any of them also exhibited the desired effects of the invention.

Industrially Applicable Field

According to the invention, a novel mixing-at the time of use-type hair-treating agent is provided. Such a composition is used for dyeing hair or bleaching hair, and particularly, the preparations before use are relatively low viscous and have stable physical properties, but when they are mixed at the time of use, the mixture exhibits such a viscosity that dropping from the hair becomes zero or is reduced (thickening), and moreover it exhibits excellent dyeing effect or bleaching effect.

Therefore, the invention can be advantageously utilized in the field of preparation of cosmetics.

We claim:

1. A mixing-at the time of use-type hair dye composition wherein a dye and an oxidizing agent are combined at the time of use, wherein
   (a) the composition after the combination comprises a dye (I), one or more (II) of surface active agents selected from the group consisting of amphoteric surface active agents and semipolar surface active agents, (II) being optional component(s), one or more (III) of higher fatty acids, one or more (IV) of anionic surface active agents, an oxidizing agent (V), and water (VII), and
   (b) before use, components selected from the group consisting of components (I), (II) and (III) are put in such a form that they each are separated from component (V).

2. A mixing-at the time of use-type hair-bleaching agent composition wherein an alkalinizing agent and an oxidizing agent are combined at the time of use, wherein
   (a) the composition after the combination comprises an alkalinizing agent (I'), one or more (II) of surface active agents selected from the group consisting of amphoteric surface active agents and semipolar surface active agents, (II) being optional component(s), one or more (III) of higher fatty acids, one or more (IV) of anionic surface active agents, an oxidizing agent (V), and water (VII), and
   (b) before use, components selected from the group consisting of components (I'), (II) and (III) are put in such a form that they each are separated from component (V).

3. The composition according to claim 1 or 2 wherein in (b), component (IV) is put in such a form that it is mixed with components (I) or (I'), (II), (III) and (VII).

4. The composition according to claim 1 or 2 wherein in (b), component (IV) is put in such a form that it is mixed with components (I) or (I'), (II), (III) and (VII), and it is also mixed with components (V) and (VII).

5. The composition according to claim 1 or 2 wherein in (b), component (IV) is put in such a form that it is mixed with components (V) and (VII).

6. A mixing-at the time of use-type hair dye composition wherein a dye and an oxidizing agent are combined at the time of use, wherein
   (a) the composition after the combination comprises a dye (I), one or more (II) of surface active agents selected from the group consisting of amphoteric surface active agents and semipolar surface active agents, (II) being optional component(s), one or more (III) of higher fatty acids, one or more (IV) of anionic surface active agents, an oxidizing agent (V), a cationic polymer (VI) and water (VII), and
   (b) before use, components selected from the group consisting of components (I), (II), (III) and (IV) are put in such a form that they are separated from components selected from the group consisting of components (V) and (VI).

7. A mixing-at the time of use-type hair-bleaching agent composition wherein an alkalinizing agent and an oxidizing agent are combined at the time of use, wherein
   (a) the composition after the combination comprises an alkalinizing agent (I'), one or more (II) of surface active agents selected from the group consisting of amphoteric surface active agents and semipolar surface active agents, (II) being optional component(s), one or more (III) of higher fatty acids, one or more (IV) of anionic surface active agents, an oxidizing agent (V), a cationic polymer (VI) and water (VII), and
   (b) before use, components selected from the group consisting of components (I'), (II), (III) and (IV) are put in a form separated from components selected from the group consisting of components (V) and (VI).

8. The composition according to any of claims 1, 2, 6 or 7 wherein the composition after the combination is adjusted to have a pH of 6 to 12.

9. The composition according to claim 1 or 2 wherein in the composition after the combination, based on its gross weight, 5 to 50 weight % of components (IV) and (II) and 0.1 to 5 weight % of component (III) are contained.

10. The composition according to claim 6 or 7 wherein in the composition after the combination, based on its gross weight, 5 to 50 weight % of components (IV) and (II), 0.1 to 5 weight % of component (III) and 0.01 to 5 weight % of component (VI) are contained.

11. The composition according to claim 1 or 2 wherein in the composition after the combination, based on its gross weight, 5 to 50 weight % of components (IV) and (II) and 0.1 to 5 weight % of component (III) are contained, and the weight ratio of component (IV)/component (II) is 4/6 to 10/0.

12. The composition according to claim 6 or 7 wherein in the composition after the combination, based on its gross weight, 5 to 50 weight % of components (IV) and (II), 0.1 to 5 weight % of component (III) and 0.01 to 5 weight % of component (VI) are contained, and the weight ratio of component (IV)/component (II) is 4/6 to 10/0.

13. The composition according to any of claims 1, 2, 6 or 7 wherein in the composition after the combination, based on its gross weight, the content of monohydric alcohols having 2 to 5 carbon atoms is 3 weight % or less.

14. The composition according to any of claims 1, 2, 6 or 7 wherein component (II) contains at least one of surface active agents selected from the group consisting of imidazolinium betaine-type amphoteric surface active agents, amidobetaine-type amphoteric surface active agents, amidosulfobetaine-type amphoteric surface active agents, betaine-type amphoteric surface active agents, sulfobetaine-type amphoteric surface active agents and tertiary amine oxide-type semipolar surface active agents.

15. The composition according to any of claims 1, 2, 6 or 7 wherein component (II) is a mixture of at least one of imidazolinium betaine-type amphoteric surface active agents with at least one member selected from the group consisting of amidobetaine-type amphoteric surface active agents, amidosulfobetaine-type amphoteric surface active agents, betaine-type amphoteric surface active agents, sulfobetaine-type amphoteric surface active agents and tertiary amine oxide-type semipolar surface active agents.

16. The composition according to any of claims 1, 2, 6 or 7 wherein component (III) contains one or more of higher fatty acids composed of a straight-chain or branched chain, saturated or unsaturated hydrocarbon having 7 to 25 carbon atoms and optionally having a hydroxyl group.

17. The composition according to any of claims 1, 2, 6 or 7 wherein component (IV) contains one or more of surface active agents selected from the group consisting of polyoxyalkylene alkyl ether sulfate salts, alkyl ether sulfate salts, α-olefinsulfonate salts and alkyloylalkyltaurine salts.

18. The composition according to any of claims 1, 2, 6 and 7 wherein component (IV) contains one or more of surface active agents selected from the group consisting of polyoxyethylene alkyl ether sulfate salts and alkyl ether sulfate salts having an alkyl chain having any even number of 10 to 18 carbon atoms.

19. The composition according to claim 6 or 7 wherein component (VI) contains one or more of polymers selected from the group consisting of quaternary nitrogen-containing cellulose derivatives, diallyldimethylammonium salt-acrylamide copolymers and poly(diallyldimethylammonium salt) derivatives.

20. The composition according to claim 1 or 2 wherein in the composition after the combination, based on its gross weight, 5 to 50 weight % of components (IV) and (II) and 0.1 to 5 weight % of component (III) are contained, and the weight ratio of component (IV)/component (II) is 4/6 to 6/4, and the pH is 8 to 12.

21. The composition according to claim 6 or 7 wherein in the composition after the combination, based on its gross weight, 5 to 50 weight % of components (IV) and (II), 0.1 to 5 weight % of component (III) and 0.01 to 5 weight % of component (VI) are contained, and the weight ratio of component (IV)/component (II) is 4/6 to 6/4, and the pH is 8 to 12.

22. The composition according to claim 1 or 2 wherein in the composition after the combination, based on its gross weight, 5 to 50 weight % of components (IV) and (II) and 0.1 to 5 weight % of component (III) are contained, and the weight ratio of component (IV)/component (II) is 4/6 to 6/4, and the pH is 6 or more and under 8.

23. The composition according to claim 6 or 7 wherein in the composition after the combination, based on its gross weight, 5 to 50 weight % of components (IV) and (II), 0.1 to 5 weight % of component (III) and 0.01 to 5 weight % of component (VI) are contained, and the weight ratio of component (IV)/component (II) is 4/6 to 6/4, and the pH is 6 or more and under 8.

24. The composition according to any of claims 1, 2, 6 or 7 wherein in the composition after the combination, the weight ratio of component (IV)/component (II) is 6/4 to 10/0, the pH is 6 to 12, and component (IV) contains one or more of surface active agents selected from the group consisting of polyoxyethylene alkyl ether sulfate salts and alkyl ether sulfate salts having an alkyl chain having any even number of 10 to 18 carbon atoms.

25. The composition according to any of claims 1, 2, 6 or 7 wherein the composition after the combination does not contain component (II), the pH is 6 to 12, and component (IV) contains one or more of surface active agents selected from the group consisting of polyoxyethylene alkyl ether sulfate salts and alkyl ether sulfate salts having an alkyl chain having any even number of 10 to 18 carbon atoms.

26. The composition according to any of claims 1, 2, 6 or 7 wherein the viscosity of the composition after the combination is 500 cps or more at 30° C.

* * * * *